(12) United States Patent
Evans-Freke

(10) Patent No.: US 7,816,323 B2
(45) Date of Patent: Oct. 19, 2010

(54) METHODS OF USING CORTICOTROPIN-RELEASING FACTOR FOR THE USE OF THE TREATMENT OF CANCER

(76) Inventor: Stephen Evans-Freke, Estate Nazareth #6L-21, St. Thomas, VI (US) 00802

(*) Notice: Subject to any disclaimer, the term of this patent is extended or adjusted under 35 U.S.C. 154(b) by 0 days.

(21) Appl. No.: 12/758,621

(22) Filed: Apr. 12, 2010

(65) Prior Publication Data

US 2010/0196389 A1 Aug. 5, 2010

Related U.S. Application Data

(63) Continuation-in-part of application No. 12/686,231, filed on Jan. 12, 2010, and a continuation-in-part of application No. 12/433,652, filed on Apr. 30, 2009.

(60) Provisional application No. 61/220,055, filed on Jun. 24, 2009, provisional application No. 61/049,292, filed on Apr. 30, 2008, provisional application No. 61/094,806, filed on Sep. 5, 2008.

(51) Int. Cl.
*A61K 38/22* (2006.01)
(52) U.S. Cl. ...................................................... 514/12
(58) Field of Classification Search .................... 514/12
See application file for complete search history.

(56) References Cited

U.S. PATENT DOCUMENTS

| | | | | |
|---|---|---|---|---|
| 2,852,054 | A * | 9/1958 | Motley | 220/834 |
| 4,312,523 | A * | 1/1982 | Haines | 40/630 |
| 2003/0061750 | A1* | 4/2003 | Bernier et al. | 40/638 |
| 2006/0163110 | A1* | 7/2006 | Adler et al. | 206/534 |

FOREIGN PATENT DOCUMENTS

WO WO 2006/021814 A2 3/2006
WO WO 2008/156719 A1 12/2008

OTHER PUBLICATIONS

MedicineNet "Cancer", accessed from http://www.medterms.com on Jun. 16, 2010, 2 pages.*
Sausville et al. Cancer Research, 2006, vol. 66, pp. 3351-3354.*
Johnson et al. British J. of Cancer, 2001, 84(10):1424-1431.*
Androulidaki et al. Mol. Cancer, 2009, vol. 8, paper No. 30, 12 pages.*
Reubi et al. J. Clin. Endocrinol. Metab., 2003, vol. 88, pp. 3312-3320.*
Tjuvajev et al. Cancer Research, 1996, vol. 56, pp. 1352-1360.*
Vredenburgh et al. Clin. Cancer Res., Feb. 15, 2007, vol. 13, No. 4, pp. 1253-1259.*
Arbiser et al., "Corticotrophin-Releasing Hormone Stimulates Angiogenesis and Epithelial Tumor Growth in the Skin," *J. Invest. Dermatology,* 1999, vol. 113, pp. 838-842.
Avastin® (bevacizumab): Solution for Intravenous Infusion, Product Label, Full Prescribing Information, May 2009.
Carlson et al., "Inhibition of Mouse Melanoma Cell Proliferation by Corticotropin-Releasing Hormone and its Analogs," *Anticancer Res.,* 2001, vol. 21, pp. 1173-1180.
Carr et al., "The Effect of Corticelin Acetate on Peritumoral Brain Edema: an Interim Report of an Open-label Study as Part of a Phase II Program," *J. Clin. Oncology,* 2007, ASCO Annual Meeting Proceedings, Part I, vol. 25, No. 18S (Jun. 20 Supplement), Abstract No. 9050.
Graziani et al., "Corticotropin-Releasing Hormone Receptor-1 in Human Endometrial Cancer," *Oncology Reports,* 2006, vol. 15, pp. 375-379.
Graziani et al., "Evidence that Corticotropin-Releasing Hormone Inhibits Cell Growth of Human Breast Cancer Cells Via the Activation of CRH-R1 Receptor Subtype," *Mol. and Cell. Endocrinology,* 2007, vol. 264, pp. 44-49.
Hariharan et al, "Phase II Randomized Dose Ranging Trial of Human Corticotropin Releasing Factor in Symptomatic Brain Tumor Patients", 2000, American Academy of Neurology 52nd Annual Meeting, Session No. 6, Neuro-Oncology: Clinical Trials, Apr. 30, 2000, Abstract S06.001.
Kesari et al., "Chapter 4: Corticosteroids in Neuro-Oncology", *Cancer Neurology in Clinical Practice: Neurologic Complications of Cancer and Its Treatment,* Second Edition, Eds. Schiff et al., Totowa, New Jersey: Human Press, 2008, pp. 47-56.
Minas et al., "Intratumoral CRH Modulates Immuno-Escape of Ovarian Cancer Cells Through FasL Regulation," *British J. Cancer,* 2007, vol. 97, pp. 637-645.
Moody et al., "Corticoptropin-Releasing Factor Stimulates Cyclic AMP, Arachidonic Acid Release, and Growth of Lung Cancer Cells," 1994, *Pepties,* vol. 15, pp. 281-285.
Tjuvajev et al., "Anti-neoplastic Properties of Human Corticotropin Releasing Factor: Involvement of the Nitric Oxide Pathway," In Vivo, 1998, vol. 12, No. 1, Jan.-Feb. 1998, pp. 1-10.
Villalona-Calero et al., "A Phase I Trial of Human Corticotropin-releasing Factor (hCRF) in Patients with Peritumoral Brain Edema," Annals of Oncology, 1998, vol. 9, pp. 71-77.
Yang et al., "Enhancement of Cell Migration by Corticotropin-Releasing Hormone Through ERK 1/2 Pathway in Murine Melanoma Cell Line, B16F10," *Experimental Dermatology,* 2006, vol. 16, pp. 22-27.
Mechtler et al., "Safety and Steroid-Sparing Potential of XERECEPT® (Corticorelin Acetate Injection) for Treatment of Peritumoral Brain Edema: an Interim Report of an Open-Label Study as Part of a Phase III Program", 2006, 11th Annual Meeting of the Society for Neuro-Oncology (SNO) Orlando, Florida (Nov. 15-19, 2006) (SNO 2006 Poster).
Mechtler et al., "The Effect of Corticorelin Acetate on Peritumoral Brain Edema: an Interim Report of an Open-Label Study as Part of a Phase III Program", 2007, 43rd Annual Meeting of the American Society of Clinical Oncology (ASCO), Chicago, Illinois (Jun. 1-5, 2007) (ASCO 2007 Poster).
Recht et al., "Long-Term Safety and Steroid-Sparing Potential of Corticorelin Acetate Injection for Treatment of Peritumoral Brain Edema: Third Interim Report of an Open-Label Study as Part of a Phase III Program", 2007, 12th Annual Meeting of the Society for Neuro-Oncology (SNO), Dallas, Texas (Nov. 15-18, 2007) (SNO 2007 Poster).

* cited by examiner

*Primary Examiner*—James D Anderson
(74) *Attorney, Agent, or Firm*—Jones Day

(57) ABSTRACT

Provided herein is a method for treating cancer in a human by administering a high dose of corticotropin-releasing factor (CRF).

15 Claims, 16 Drawing Sheets

Drugs and Treatment (Colo205-e257)

| Gr. | N | 1 Drug/Testing Agent | | | | | | 2 Drug/Testing Agent | | | | | |
|---|---|---|---|---|---|---|---|---|---|---|---|---|---|
| | | Agent | Vehicle | mg/kg | Route | Schedule | | Agent | Vehicle | mg/kg | Route | Schedule |
| 1 | 10 | Vehicle | | - | sc | bid | | - | | - | - | - |
| 2 | 10 | SB1 | | 100* | sc | bid | | - | | - | - | - |
| 3 | 10 | SB1 | | 200* | sc | bid | | - | | - | - | - |
| 4 | 10 | bevacizumab | | 5 | ip | biwk to end | | - | | - | - | - |
| 5 | 10 | SB1 | | 200* | sc | bid | | bevacizumab | | 5 | ip | biwk to end |

Colo205-e257 Response Summary for Day 20 (TV = 1000 mm³ or Day 60, MTV on day 1 for Group 1: vehicle = 166.75)

| | | Treatment Regimen 1 | | | | Median TTE | TC | % TGD | Stat Sign | MTV (n), Day 20 | PR | CR | TFS | BW Nadir | TR | NTRm | NTR |
|---|---|---|---|---|---|---|---|---|---|---|---|---|---|---|---|---|---|
| Gr. | n | Agent | mg/kg | Route | Schedule | | | | | | | | | | | | |
| 1# | 10 | Vehicle | - | - | - | 20. | -- | -- | | | | | | - | | | NTR |
| 2 | 10 | SB1 | 100* | sc | bid | 20 | 0 | 0 | | 600(10) | 0 | 0 | 0 | 0.5%(2) | 0 | 0 | 0 |
| 3 | 10 | SB1 | 200* | sc | bid | 20 | 0 | 0 | | 527(9) | 0 | 0 | 0 | -0.6% (2) | 0 | 0 | 0 |
| 4 | 10 | bevacizumab | 5 | ip | biwk to end | 20 | 0 | 0 | | 446(8) | 0 | 0 | 0 | -0.8% (2) | 1 | 0 | 0 |
| 5 | 10 | SB1 | 200* | sc | bid | 20 | 0 | 0 | | 320(10) | 0 | 0 | 0 | - | 0 | 0 | 0 |
| | | | | | | | | | | 196(10) | | | | -3.6% (13) | | | |

| | | Treatment Regimen 2 | | | | Median TTE | TC | % TGD | Stat Sign | MTV (n), Day 20 | PR | CR | TFS | BW Nadir | TR | NTRm | NTR |
|---|---|---|---|---|---|---|---|---|---|---|---|---|---|---|---|---|---|
| Gr. | n | Agent | mg/kg | Route | Schedule | | | | | | | | | | | | |
| 1# | 10 | - | - | - | - | 20. | -- | -- | | | | | | - | | | NTR |
| 2 | 10 | - | - | - | - | 20 | 0 | 0 | | 600(10) | 0 | 0 | 0 | 0.5%(2) | 0 | 0 | 0 |
| 3 | 10 | - | - | - | - | 20 | 0 | 0 | | 527(9) | 0 | 0 | 0 | -0.6% (2) | 0 | 0 | 0 |
| 4 | 10 | - | - | - | - | 20 | 0 | 0 | | 446(8) | 0 | 0 | 0 | -0.8% (2) | 1 | 0 | 0 |
| 5 | 10 | bevacizumab | 5 | ip | biwk to end | 20 | 0 | 0 | | 320(10) | 0 | 0 | 0 | - | 0 | 0 | 0 |
| | | | | | | | | | | 196(10) | | | | -3.6% (13) | | | |

\# - Control Group    * -μg/kg

Figure 4D

Drugs and Treatment (H1299-e271)

| Gr. | N | 1 Drug/Testing Agent ||||| 2 Drug/Testing Agent |||||
| | | Agent | Vehicle | mg/kg | Route | Schedule | Agent | Vehicle | mg/kg | Route | Schedule |
|---|---|---|---|---|---|---|---|---|---|---|---|
| 1 | 10 | Vehicle | | - | sc | bid | - | - | - | - | - |
| 2 | 10 | SB1 | | 100* | sc | bid | - | - | - | - | - |
| 3 | 10 | SB1 | | 200* | sc | bid | - | - | - | - | - |
| 4 | 10 | bevacizumab | | 5 | ip | biwk to end | - | - | - | - | - |
| 5 | 10 | SB1 | | 200* | sc | bid | bevacizumab | | 5 | ip | biwk to end |

H1299-e271 Response Summary for Day 20 (TV = 2000 mm³ or Day 60, MTV on day 1 for Group 1: vehicle = 100)

Treatment Regimen 1

| Gr. | n | Agent | mg/kg | Route | Schedule | Median TTE | TC | % TGD | Stat Sign | MTV (n), Day 20 | PR | CR | TFS | BW Nadir | TR | NTRm | NTR |
|---|---|---|---|---|---|---|---|---|---|---|---|---|---|---|---|---|---|
| 1# | 10 | Vehicle | - | | | 20. | -- | - | | | 0 | 0 | 0 | - | | | |
| 2 | 10 | SB1 | 100* | sc | bid | 20 | 0 | 0 | | 1324(6) | 0 | 0 | 0 | 0.5%(2) | 0 | 0 | 0 |
| 3 | 10 | SB1 | 200* | sc | bid | 20 | 0 | 0 | | 1183(9) | 0 | 0 | 0 | -0.6% (2) | 0 | 0 | 0 |
| 4 | 10 | bevacizumab | 5 | ip | biwk to end | 20 | 0 | 0 | | 1080(6) | 0 | 0 | 0 | -0.8% (2) | 1 | 0 | 0 |
| 5 | 10 | SB1 | 200* | sc | bid | 20 | 0 | 0 | | 1044(10) | 0 | 0 | 0 | -- | 0 | 0 | 0 |
|  |  |  |  |  |  |  |  |  |  | 650(8) |  |  |  | -3.6% (13) | 0 | 0 | 0 |

Treatment Regimen 2

| Gr. | n | Agent | mg/kg | Route | Schedule | Median TTE | TC | % TGD | Stat Sign | MTV (n), Day 20 | PR | CR | TFS | BW Nadir | TR | NTRm | NTR |
|---|---|---|---|---|---|---|---|---|---|---|---|---|---|---|---|---|---|
| 1# | 10 | - | - | - | - | 20. | -- | - | | | 0 | 0 | 0 | - | | | |
| 2 | 10 | - | - | - | - | 20 | 0 | 0 | | 1324(6) | 0 | 0 | 0 | 0.5%(2) | 0 | 0 | 0 |
| 3 | 10 | - | - | - | - | 20 | 0 | 0 | | 1183(9) | 0 | 0 | 0 | -0.6% (2) | 0 | 0 | 0 |
| 4 | 10 | - | - | - | - | 20 | 0 | 0 | | 1080(6) | 0 | 0 | 0 | -0.8% (2) | 1 | 0 | 0 |
| 5 | 10 | bevacizumab | 5 | ip | biwk to end | 20 | 0 | 0 | | 1044(10) | 0 | 0 | 0 | -- | 0 | 0 | 0 |
|  |  |  |  |  |  |  |  |  |  | 650(8) |  |  |  | -3.6% (13) | 0 | 0 | 0 |

\# - Control Group   * -µg/kg

Figure 5D

Drugs and Treatment (MX-1-e247)

| | | 1 Drug/Testing Agent | | | | | 2 Drug/Testing Agent | | | | |
|---|---|---|---|---|---|---|---|---|---|---|---|
| Gr. | N | Agent | Vehicle | mg/kg | Route | Schedule | Agent | Vehicle | mg/kg | Route | Schedule |
| 1 | 10 | Vehicle | | - | sc | bid | - | - | - | - | - |
| 2 | 10 | SB1 | | 100* | sc | bid | - | - | - | - | - |
| 3 | 10 | SB1 | | 200* | sc | bid | - | - | - | - | - |
| 4 | 10 | bevacizumab | | 5 | ip | biwk to end | - | - | - | - | - |
| 5 | 10 | SB1 | | 200* | sc | bid | bevacizumab | | 5 | ip | biwk to end |

MX-1-e247 Response Summary for Day 27 (TV = 1500 mm³ or Day 60, MTV on day 1 for Group 1: vehicle = 126)

Treatment Regimen 1

| Gr. | n | Agent | mg/kg | Route | Schedule | Median TTE | TC | % TGD | Stat Sign | MTV (n), Day 20 | PR | CR | TFS | BW Nadir | TR | NTRm | NTR |
|---|---|---|---|---|---|---|---|---|---|---|---|---|---|---|---|---|---|
| 1# | 10 | Vehicle | - | | | 19.8 | -- | -- | | | 0 | 0 | 0 | - | | | NTR |
| 2 | 10 | SB1 | 100* | sc | bid | 23 | 3.2 | 16 | | 1166(10) | 0 | 0 | 0 | -0.5%(2) | 0 | 0 | 0 |
| 3 | 10 | SB1 | 200* | sc | bid | 27 | 3.2 | 36 | | 1437(3) | 0 | 0 | 0 | -0.6% (2) | 0 | 0 | 0 |
| 4 | 10 | bevacizumab | 5 | ip | biwk to end | 27 | 3.2 | 36 | | 847(5) | 0 | 0 | 0 | -0.8% (2) | 1 | 0 | 0 |
| | | | | | | | | | | 756(6) | | | | -- | | | |
| 5 | 10 | SB1 | 200* | sc | bid | 27 | 3.2 | 36 | | 405(7) | 0 | 0 | 0 | -3.6% (13) | 0 | 0 | 0 |

Treatment Regimen 2

| Gr. | n | Agent | mg/kg | Route | Schedule | Median TTE | TC | % TGD | Stat Sign | MTV (n), Day 20 | PR | CR | TFS | BW Nadir | TR | NTRm | NTR |
|---|---|---|---|---|---|---|---|---|---|---|---|---|---|---|---|---|---|
| 1# | 10 | - | - | - | - | 19.8 | -- | -- | | | 0 | 0 | 0 | - | | | NTR |
| 2 | 10 | - | - | - | - | 23 | 3.2 | 16 | | 1166(10) | 0 | 0 | 0 | -0.5%(2) | 0 | 0 | 0 |
| 3 | 10 | - | - | - | - | 27 | 3.2 | 36 | | 1437(3) | 0 | 0 | 0 | -0.6% (2) | 0 | 0 | 0 |
| 4 | 10 | - | - | - | - | 27 | 3.2 | 36 | | 847(5) | 0 | 0 | 0 | -0.8% (2) | 1 | 0 | 0 |
| | | | | | | | | | | 756(6) | | | | -- | | | |
| 5 | 10 | bevacizumab | 5 | ip | biwk to end | 27 | 3.2 | 36 | | 405(7) | 0 | 0 | 0 | -3.6% (13) | 0 | 0 | 0 |

- Control Group  * -µg/kg

Figure 6D

Legend of Figures 4D, 5D, and 6D

| Median TTE | - | Median Time to Endpoint | TFS | - | No. of Tumor Free Survivors |
|---|---|---|---|---|---|
| Stat Sign | - | Statistical Significance | BW Nadir | - | Lowest Mean Body Weight for Group (based on at least half of the remaining animals, expressed as % of initial mean BW) |
| MTV (n) | - | Median Tumor Volume (number of animals used for calculation) | TR | - | No. of Treatment-related Deaths |
| PR | - | No. of Partial Regressions | NTRm | - | No. of Non-treatment-related Deaths, due to Metastasis |
| CR | - | No. of Complete Regressions | NTR | - | No. of Non-treatment-related Deaths, due to Accident/Unknown Etiology |

Figure 7

METHODS OF USING CORTICOTROPIN-RELEASING FACTOR FOR THE USE OF THE TREATMENT OF CANCER

1. PRIORITY

This application is a continuation-in-part of U.S. patent application Ser. No. 12/686,231, filed on Jan. 12, 2010, which itself claims the benefit of U.S. Provisional Application No. 61/220,055, filed on Jun. 24, 2009. U.S. patent application Ser. No. 12/686,231 is a continuation-in-part of U.S. patent application Ser. No. 12/433,652, filed on Apr. 30, 2009, which itself claims the benefit of U.S. Provisional Application No. 61/049,292, filed on Apr. 30, 2008, and U.S. Provisional Application No. 61/094,806, filed on Sep. 5, 2008. The applications cited above are herein incorporated by reference into the specification to the same extent as if each individual patent application was specifically and individually indicated to be incorporated herein by reference.

2. FIELD

Provided herein are methods for use of corticotropin-releasing factor (CRF) for the treatment of cancer.

3. BACKGROUND

There are many compositions known in the art for the treatment of cancer.

4. SUMMARY OF THE DISCLOSURE

Applicants have determined that CRF alone can surprisingly have a beneficial effect for treatment of tumors. Prior uses of CRF include a study examining the use of CRF as an adjuvant to dexamethasone to reduce brain edema. The study concluded that "[c]orticorelin acetate treatment was associated with reduced exposure to dexamethasone and improvement in steroid-related side effects in patients [with] perituomoral edema." (Mechtler et al., 11th Annual Meeting of the Society For Neuro-Oncology (SNO) Orlando, Fla., Nov. 15-19, 2006 and Mechtler et al. 43rd Annual Meeting of the American Society of Clinical Oncology (ASCO), Chicago, Ill., Jun. 1-5, 2007). Unlike the prior uses of CRF, the Applicants have found that CRF alone can prevent the development or growth of a tumor and may even reduce the size of a tumor. In particular, Applicants found that patients treated with CRF alone not only maintained tumor size, but also exhibited reduction in size of brain tumors, and exhibited prolonged survival rates. Applicants also found that patients with metastatic tumors were particularly responsive to treatment with CRF. Applicants have also found that CRF, when used in combination with one or more agents, such as an angiogenesis inhibitor, such as bevacizumab (Avastin®) or sunitinib malate (Sutent®), is effective preventing the development or growth of a tumor and may even reduce the size of a tumor.

Thus, in a first aspect, provided herein are methods for treating or managing cancer by administering CRF to a human subject. As used herein, the term "cancer" refers to a neoplasm or tumor resulting from abnormal uncontrolled growth of cells. Non-limiting examples include those cancers described in Section 4, infra. The term "cancer" encompasses a disease involving both pre-malignant and malignant cancer cells. In some embodiments, cancer refers to a localized overgrowth of cells that has not spread to other parts of a subject, e.g., a benign or malignant tumor. As used herein "subject" is a human, such as a patient. In other embodiments, cancer refers to a malignant tumor which has invaded and destroyed neighboring body structures and spread to distant sites. As used herein, the terms "treat", "treating" or "treatment of" mean that the severity of a subject's condition is reduced or at least partially improved or ameliorated and/or that some alleviation, mitigation or decrease in at least one clinical symptom is achieved and/or there is an inhibition or delay in the progression of the condition and/or delay in the progression of disease or illness. As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

In a related aspect, the methods of the disclosure can be used to prevent tumor progression. As used herein and unless otherwise indicated, the term "tumor progression" encompasses continued tumor growth, an increase in tumor size or volume, and/or formation of metastases. As used herein and unless otherwise indicated, the term "preventing tumor progression" and any grammatical equivalents thereof mean that the tumor growth is inhibited, stopped or reversed, that the size or volume of the tumor remains the same or decreases, and/or that no additional metastases of the tumor are formed in other parts of the body. The term further may also include to mean lengthening the time that a patient who had suffered from a tumor remains in remission, reducing mortality rates of tumor patients, preventing the worsening of a symptom associated with the tumor, and/or maintaining a reduction in severity or avoidance of a symptom associated with the tumor.

In one aspect, provided herein is a method for preventing tumor progression in a human, by administering for more than three days, a composition comprising CRF at a total daily dose no less than about 1 mg, to a human diagnosed with or potentially having the tumor. In another aspect, provided herein is a method for preventing tumor progression in a human, by administering for more than three days, a composition comprising CRF, wherein CRF is administered at a dose effective to inhibit tumor progression, to a human diagnosed with or potentially having the tumor. As used herein and unless otherwise indicated the term "a human diagnosed with a tumor" refers to a human in which a neoplastic growth of a tissue which may be either benign or malignant exists and/or has been detected. In some embodiments, the term refers to a cancer patient. As used herein and unless otherwise indicated the term "a human that potentially has a tumor" refers to a human showing symptoms or abnormal tissue growth that are associated with a tumor, in such a human the tumor may have been detected or a physician has reasonable belief that the tumor exists based on clinical presentation.

In another aspect, the invention features a method of preventing tumor progression in a human by administering a composition comprising CRF to a human having metastatic disease. In another aspect, the invention features a method of prophylactically preventing the development of metastasis in a human by administering a composition comprising CRF to a human.

Further, provided herein is a treatment regimen for prevention of tumor progression in a human, by administering for more than three days, a composition comprising CRF, to a human potentially having the tumor; and monitoring tumor progression in the human. As used herein and unless otherwise indicated, the term "monitoring" refers to methods that can be used to determine tumor growth, an increase in tumor size or volume, and/or formation of metastases. These methods comprise imaging technologies including X-ray radiography, computer tomography, and magnetic resonance imaging (MRI); the detection of biomarkers; biopsy procedures; and any other method known to a person of skill in the art, which may be used to determine tumor growth, an increase in tumor size or volume, and/or formation of metastases.

In another aspect, the invention features a method for treating malignant tumors in humans comprising administering CRF such that the biological activity of the tumor is altered. Examples of the biological activity of the tumor that may be altered in accordance with the invention include, but are not limited to, hormone production, stimulation of angiogenesis, tumor growth, metabolic activity, cytokine production, immunogenicity, stimulating localized fluid accumulation, alteration of extracellular matrix, including cartilage, rate of cell division, production of toxins and other cytotoxic molecules, and alteration of apoptosis.

In accordance with any of the methods provided herein, CRF can be administered over a period of time that exceeds three days, such as for five days or more, for seven to fourteen days or more, for two or three weeks or more, or for a year or more.

In accordance with the disclosure, CRF can be administered continuously over that time or may be administered intermittently over that time. The administered dose of CRF can be delivered as a single dose (e.g., a single bolus injection) or intermittently by multiple injections or infusions. Alternatively, the administered dose of CRF is delivered over a period of time (e.g., continuous infusion).

Administration of CRF may be continued or repeated until the patient experiences stable disease or regression, or until the patient experiences disease progression or unacceptable toxicity.

CRF can be administered either subcutaneously or intravenously. In one embodiment, CRF is administered intravenously. In some embodiments, CRF is administered by intravenous infusion at a rate of 0.01 µg/kg/hr to 40 µg/kg/hr; 0.05 µg/kg/hr to 30 µg/kg/hr; 1.0 µg/kg/hr to 20 µg/kg/hr; 2 µg/kg/hr to 15 µg/kg/hr and 5 µg/kg/hr to 10 µg/kg/hr. In other embodiments, CRF is administered by subcutaneous injection. The amount of CRF injected may vary. In certain embodiments, the amount of CRF administered subcutaneously or intravenously may be in the range of 0.01 µg/kg/hr to 1 mg/kg/hr; 0.05 µg/kg/hr to 500 µg/kg/hr; 1.0 µg/kg/hr to 200 µg/kg/hr; 2 µg/kg/hr to 150 µg/kg/hr; 5 µg/kg/hr to 100 µg/kg/hr; 10 µg/kg/hr to 150 µg/kg/hr; 20 µg/kg/hr to 100 µg/kg/hr; 30 µg/kg/hr to 50 µg/kg/hr; 20 µg/kg/hr to 30 µg/kg/hr; and 10 µg/kg/hr to 15 µg/kg/h. In certain embodiments, the amount of CRF administered subcutaneously, intravenously, topically, intradermally, transdermally, intranasally, or via pulmonary can be 1 µg/kg, 2 µg/kg, 3 µg/kg, 4 µg/kg, 5 µg/kg, 6 µg/kg, 10 µg/kg, 15 µg/kg, 20 µg/kg, 30 µg/kg, 40 pig/kg, 50 pig/kg, 60 µg/kg, 70 µg/kg, 80 µg/kg, 90 µg/kg, 100 µg/kg, 200 µg/kg, 300 µg/kg, 400 µg/kg, 500 µg/kg, 600 µg/kg, 700 µg/kg, 800 µg/kg, 900 µg/kg, and 1 mg/kg.

CRF can also be administered via subcutaneous, intravenous, topical, intradermal, transdermal, intranasal, or via pulmonary routes.

The total daily dose of CRF administered to a patient diagnosed with a tumor may exceed 100 mg. In some embodiments, the total daily dose of CRF is in the range of 0.1 mg to 20 mg. In some embodiments, the total daily dose of CRF is in the range of 1 mg to 20 mg. In certain embodiments, the total daily dose of CRF is in the range of 2.5 mg to 10 mg. In certain embodiments, the total daily dose of CRF is in the range of 4 mg to 10 mg.

CRF may be administered in combination with another drug ("second active agent") or another therapy for treating or managing cancer. In one embodiment, the second active agent is an angiogenesis inhibitor.

In one embodiment, the second active agent is the angiogenesis inhibitor bevacizumab (Avastin®). In various embodiments, CRF is administered with bevacizumab (Avastin®) for treatment of cancer of the colon or rectum, such as metastatic colorectal cancer; lung cancer, such as non-squamous non-small cell lung cancer; breast cancer, such as metastatic breast cancer or metastatic HER2-negative breast cancer; brain cancer, such as glioma, adult glioblastoma, pediatric glioblastoma, pediatric resistant glioblastoma, and pediatric medulloblastoma; and or renal cancer, such as advanced renal cell carcinoma.

In another embodiment, the second active agent is the angiogenesis inhibitor sunitinib malate (Sutent®). In various embodiments, CRF is administered with sunitinib malate (Sutent®) for treatment of renal cancer, such as advanced renal cell carcinoma; cancer of the colon or rectum, such as metastatic colorectal cancer; lung cancer, such as non-squamous non-small cell lung cancer; breast cancer, such as metastatic breast cancer or metastatic HER2-negative breast cancer; or brain cancer, such as glioma, adult glioblastoma, pediatric glioblastoma, pediatric resistant glioblastoma, and pediatric medulloblastoma.

In another aspect, the invention features a method for preventing tumor progression in a subject having cancer, comprising administering CRF and an angiogenesis inhibitor, such as bevacizumab (Avastin®) or sunitinib malate (Sutent®), to said subject, wherein tumor progression in the subject is monitored or the administration of CRF and an angiogenesis inhibitor results in a maintenance or decrease in the size of the tumor. In another aspect, the invention features a method for treating human subjects having cancer, comprising administering CRF and an angiogenesis inhibitor, such as bevacizumab (Avastin®) or sunitinib malate (Sutent®), to said human subjects in an amount effective to result in the maintenance or decrease in the size of the tumor in at least 10% of the human subjects. In another aspect, the invention features a method for treating a human subject having cancer, comprising administering CRF in an amount of about 1 mg; 2 mg; 3 mg; 4 mg; 5 mg; 6 mg; 7 mg; 8 mg; 9 mg; or 10 mg, once or twice daily and an angiogenesis inhibitor, such as bevacizumab (Avastin®) at a dose of 5 mg/kg or 15 mg/kg, once a week, every two weeks or every three weeks; or sunitinib malate (Sutent®), at a dose of 12.5 mg; 25 mg; or 50 mg taken once daily. In another aspect, the invention features a method for preventing tumor progression in a subject having cancer, comprising administering CRF and an angiogenesis inhibitor, such as bevacizumab (Avastin®) or sunitinib malate (Sutent®), to said subject, wherein CRF and the angiogenesis inhibitor are administered at a therapeutically effective dose to inhibit tumor progression; and wherein, when tested in an animal model, the effect of administering a combination of said CRF and said angiogenesis inhibitor on inhibiting tumor progression is greater than administering either said CRF or said angiogenesis inhibitor alone. In another aspect, the invention features a method for preventing tumor progression in a subject having cancer, comprising administering CRF and an angiogenesis inhibitor, such as bevacizumab (Avastin®) or sunitinib malate (Sutent®), to said subject, wherein said cancer is breast, lung, colon, or renal cancer.

In another aspect, the invention features a method for preventing tumor progression in a subject having cancer, comprising administering CRF and an angiogenesis inhibitor, such as bevacizumab (Avastin®) or sunitinib malate (Sutent®), to said subject, wherein tumor progression in the subject is monitored or the administration of CRF and an angiogenesis inhibitor results in a maintenance or decrease in the size of the tumor, and wherein the CRF has an angiogenesis inhibitor-sparing effect. In another aspect, the invention features a method for preventing tumor progression in a subject having cancer, comprising administering CRF and an angiogenesis inhibitor, such as bevacizumab (Avastin®) or sunitinib malate (Sutent®), to said subject, wherein tumor progression in the subject is monitored or the administration of CRF and an angiogenesis inhibitor results in a maintenance or decrease in the size of the tumor, and wherein the amount of bevacizumab (Avastin®) or sunitinib malate (Sutent®) administered is less than an amount of bevacizumab (Avastin®) or sunitinib malate (Sutent®) for preventing tumor progression in a subject having cancer when administered alone. In another aspect, the invention features a method for treating a human subject having cancer comprising administering CRF in an amount of about 1 mg; 2 mg; 3 mg; 4 mg; 5 mg; 6 mg; 7 mg; 8 mg; 9 mg; or 10 mg, once or twice daily and an angiogenesis inhibitor, such as bevacizumab (Avastin®) at a dose of 0.1 mg/kg; 0.5 mg/kg; 1 mg/kg; 2.5 mg/kg; or 5 mg/kg, once a week, every two weeks or every three weeks; or sunitinib malate (Sutent®), at a dose of 1 mg; 5 mg; or 10 mg taken once daily. In another aspect, the invention features a method for preventing tumor progression in a subject having cancer, comprising administering CRF and an angiogenesis inhibitor, such as bevacizumab (Avastin®) or sunitinib malate (Sutent®), to said subject, wherein CRF and the angiogenesis inhibitor are administered at a therapeutically effective dose to inhibit tumor progression; and wherein, when tested in an animal model, the effect of administering a combination of said CRF and said angiogenesis inhibitor on inhibiting tumor progression is greater than administering either said CRF or said angiogenesis inhibitor alone, and wherein the CRF has an angiogenesis inhibitor-sparing effect. In another aspect, the invention features a method for preventing tumor progression in a subject having cancer, comprising administering CRF and an angiogenesis inhibitor, such as bevacizumab (Avastin®) or sunitinib malate (Sutent®), to said subject, wherein said cancer is breast, lung, colon, or renal cancer, and wherein the CRF has an angiogenesis inhibitor-sparing effect.

In another aspect, the invention features a container for a pharmaceutical composition comprising CRF and a pharmaceutical label, wherein the pharmaceutical label indicates that the CRF is to be administered with an angiogenesis inhibitor, such as bevacizumab (Avastin®) or sunitinib malate (Sutent®), for treatment of cancer. In one embodiment, the dose of CRF administered is between 50 µg/kg to 300 µg/kg of body weight of a subject. In a particular embodiment, the dose of CRF administered is 100 µg/kg of body weight of a subject. In a particular embodiment, the dose of CRF administered is 200 µg/kg of body weight of a subject. In one embodiment, the pharmaceutical label indicates that the bevacizumab (Avastin®) is to be administered at a dose range between 5 mg/kg and 15 mg/kg of body weight of a subject once a week, every two weeks or every three weeks. In one particular embodiment, the pharmaceutical label indicates that the bevacizumab (Avastin®) is to be administered at a dose of 10 mg/kg of body weight of a subject. In one embodiment, the pharmaceutical label indicates that Sutent® is administered at a dose of 12.5 mg; 25 mg or 50 mg taken once daily.

CRF may be administered in combination with one or more drugs or one or more therapies for treating or managing cancer. In one embodiment, CRF is administered with bevacizumab (Avastin®) and one or more drugs or one or more therapies for treating or managing cancer, such as chemotherapy. In one embodiment, CRF is administered with sunitinib malate (Sutent®) and one or more drugs or one or more therapies for treating or managing cancer, such as chemotherapy.

In a specific embodiment, the tumor is a brain tumor. The brain tumor may be a glioblastoma (both adult and pediatric), pediatric resistant glioblastoma, glioma, ependymoma, astrocytoma, medulloblastoma, pediatric medulloblastoma, neuroglioma, oligodendroglioma or meningioma. Alternatively, the brain tumor may be a secondary brain tumor or a brain metastasis.

Other cancers and tumors that can be treated in accordance with the methods provided herein include, but are not limited to bladder cancer, breast cancer, cervical cancer, colon cancer (including colorectal cancer), esophageal cancer, gastric cancer, head and neck cancer, liver cancer, lung cancer (both small cell and non-small cell), squamous non-small cell lung cancer, melanoma, myeloma, neuroblastoma, ovarian cancer, pancreatic cancer, prostate cancer, renal cancer, advanced renal carcinoma, sarcoma (including osteosarcoma), skin cancer (including squamous cell carcinoma), stomach cancer, testicular cancer, thyroid cancer, and uterine cancer. In one embodiment, the methods encompass treating or managing colon, pancreas, breast, mesothelioma, cholangiocarcinoma, leiomyosarcoma, liposarcoma, melanoma, nasopharyngeal, neuroendocrine, ovarian, renal, salivary gland, small cell lung cancer, or spindle cell carcinoma.

In some embodiments, the methods described herein may include treating a metastasis resulting from bladder cancer, breast cancer (including metastatic HER2-negative breast cancer), cervical cancer, colon cancer (including colorectal cancer), esophageal cancer, head and neck cancer, liver cancer, lung cancer (both small cell and non-small cell), melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, uterine cancer, mesothelioma, cholangiocarcinoma, leiomyosarcoma, liposarcoma, nasopharyngeal cancer, neuroendocrine cancer, ovarian cancer, renal cancer, salivary gland cancer, small cell lung cancer, or spindle cell carcinoma. In some embodiments, the methods described herein may include treating a metastatic brain tumor resulting from bladder cancer, breast cancer, cervical cancer, colon cancer (including colorectal cancer), esophageal cancer, head and neck cancer, liver cancer, lung cancer (both small cell and non-small cell), non-squamous non-small cell lung cancer, melanoma, myeloma, neuroblastoma, ovarian cancer, pancreatic cancer, prostate cancer, renal cancer, advanced renal cell carcinoma, sarcoma (including osteosarcoma), skin cancer (including squamous cell carcinoma), stomach cancer, testicular cancer, thyroid cancer, uterine cancer, mesothelioma, cholangiocarcinoma, leiomyosarcoma, liposarcoma, nasopharyngeal cancer, neuroendocrine cancer, ovarian cancer, renal cancer, salivary gland cancer, small cell lung cancer, or spindle cell carcinoma.

Methods also include prophylactic methods to prevent metastasis resulting from bladder cancer, breast cancer, cervical cancer, colon cancer (including colorectal cancer), esophageal cancer, head and neck cancer, liver cancer, lung cancer (both small cell and non-small cell), non-squamous non-small cell lung cancer, melanoma, myeloma, neuroblastoma, ovarian cancer, pancreatic cancer, prostate cancer, renal cancer, advanced renal cell carcinoma, sarcoma (including osteosarcoma), skin cancer (including squamous cell carcinoma), stomach cancer, testicular cancer, thyroid cancer, uterine cancer, mesothelioma, cholangiocarcinoma, leiomyosarcoma, liposarcoma, nasopharyngeal cancer, neuroendocrine cancer, ovarian cancer, renal cancer, salivary gland cancer, small cell lung cancer, or spindle cell carcinoma. Methods also include prophylactic methods to prevent metastasis of a brain tumor resulting from bladder cancer, breast cancer, cervical cancer, colon cancer (including colorectal cancer), esophageal cancer, head and neck cancer, liver cancer, lung cancer (both small cell and non-small cell), non-squamous non-small cell lung cancer, melanoma, myeloma, neuroblastoma, ovarian cancer, pancreatic cancer, prostate cancer, renal cancer, advanced renal cell carcinoma, sarcoma (including osteosarcoma), skin cancer (including squamous cell carcinoma), stomach cancer, testicular cancer, thyroid cancer, uterine cancer, mesothelioma, cholangiocarcinoma, leiomyosarcoma, liposarcoma, nasopharyngeal cancer, neuroendocrine cancer, ovarian cancer, renal cancer, salivary gland cancer, small cell lung cancer, or spindle cell carcinoma.

In some embodiments, the tumor or cancer to be treated has relapsed or recurred. The term "relapsed" or "recurred" refers to a situation where patients who have had a remission of cancer after therapy have a return of cancer cells.

In other embodiments, the tumor or cancer to be treated has become refractory or resistant. The term "refractory" or "resistant" refers to a circumstance where patients, even after intensive treatment, have residual cancer cells in their body.

In some embodiments, the tumor or cancer to be treated has not previously been treated, so that the administration of CRF with an angiogenesis inhibitor is a first line treatment.

In certain embodiment, the methods described herein may comprise administering CRF conjugated to a biopolymer or biocompatible polymer. As used herein, the term "CRF conjugate" refers to a CRF polypeptide that has been modified to include a moiety that results in an improved pharmacokinetic profile as compared to unmodified CRF. The improvement in the pharmacokinetic profile may be observed as an improvement in one or more of the following parameters: potency, stability, area under the curve and circulating half life. In a specific embodiment, CRF is conjugated to polyethylenglycol (PEG).

5. BRIEF DESCRIPTION OF THE DRAWINGS

FIG. 4A shows a table, which shows the number of mice, agent(s), dose, route of administration, schedule, for each of the groups of mice in a study analyzing the effect of administration of CRF, bevacizumab (Avastin®), or CRF and bevacizumab (Avastin®) on human colon tumor cell growth in mice.

FIG. 4D shows a table summarizing the response for day 20 of groups of mice involved in a study analyzing the effect of administration of CRF, bevacizumab (Avastin®), or CRF and bevacizumab (Avastin®) on human colon tumor cell growth. Legend provided in FIG. 7.

FIG. 5A shows a table, which shows the number of mice, agent(s), dose, route of administration, schedule, for each of the groups of mice in a study analyzing the effect of administration of CRF, bevacizumab (Avastin®), or CRF and bevacizumab (Avastin®) on human non-small cell lung carcinoma tumor cell growth in mice.

FIG. 5D shows a table summarizing the response for day 20 of groups of mice involved in a study analyzing the effect of administration of CRF, bevacizumab (Avastin®), or CRF and bevacizumab (Avastin®) on human non-small cell lung carcinoma tumor cell growth. Legend provided in FIG. 7.

FIG. 6A shows a table, which shows the number of mice, agent(s), dose, route of administration, schedule, for each of the groups of mice in a study analyzing the effect of administration of CRF, bevacizumab (Avastin®), or CRF and bevacizumab (Avastin®) on human breast carcinoma cell growth in mice.

FIG. 6D is a table summarizing the response for day 27 of groups of mice involved in a study analyzing the effect of administration of CRF, bevacizumab (Avastin®), or CRF and bevacizumab (Avastin®) on human breast carcinoma cell growth. Legend provided in FIG. 7.

6. DETAILED DESCRIPTION

6.1 Corticotropin-Releasing Factor

Figure 1:
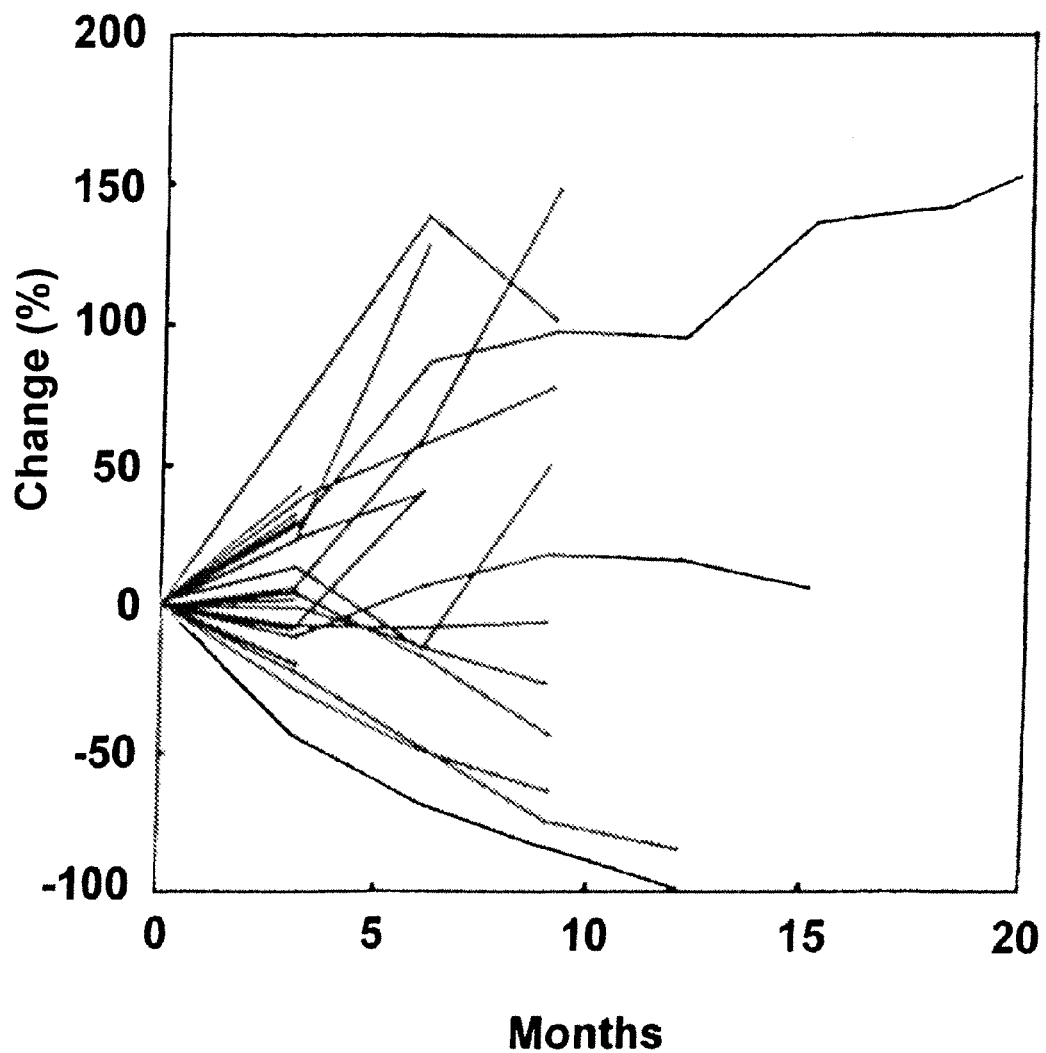
FIG. 1 shows a graph of the percent change in brain tumor size as measured by MRI in brain cancer patients receiving 2 mg/day (1 mg dose, twice daily) of human CRF subcutaneously for at least 3-6 months.

Corticotropin-Releasing Factor (CRF) is an endogenous 41 amino acid peptide first identified in 1981 as the major hypothalamic hormone responsible for stimulation of the pituitary-adrenal axis (Vale, W., et al., *Science* 213:1394-

1397 (1981)). In certain embodiments, the CRF peptides employed in the formulations of the instant disclosure are synthesized using solid- or solution-phase peptide synthesis techniques. However, other sources of the CRF peptide are readily available to the ordinarily skilled artisan. The terms "corticotropin releasing factor" and "CRF" likewise cover biologically active CRF equivalents; e.g., peptides differing in one or more amino acids in the overall amino acid sequence as well as substitutional, deletional, insertional and modified amino acid variants of CRF which substantially retain the biological activity normally associated with the intact CRF peptide.

CRF can be obtained from natural sources, expressed recombinantly, or produced synthetically. CRF is also known in the art as corticotrop(h)in-releasing hormone (CRH), corticoliberin, corticorelin and CRF-41. As used herein, the terms "corticotropin releasing factor", "CRF", "corticotrop (h)in-releasing hormone", "CRH", "corticoliberin", "corticorelin", "CRF-41" or grammatical equivalents thereof have a functional definition and refer to peptides which share one or more of the biological activities of the native, intact CRF peptide. Such biological activities include, for example, the ability to stimulate the release of ACTH, the ability to inhibit edema in vivo and the ability to bind to CRF receptors, including CRF Receptor 1 and CRF Receptor 2. Each of the above terms is intended to denote the 41 amino acid human, rat, ovine, sheep, goat, porcine, and fish corticotropin releasing factor peptides and CRF peptides from other mammals, whether isolated from natural source extraction and purification, from recombinant cell culture systems or synthesized using peptide synthesis technology. These terms are also intended to denote other CRF-related peptides which share one or more of the biological activities of the native CRF peptides such as urocortin (Vaughan, J., et al., *Nature* 378: 287-292 (1995), Donaldson, C. J., et al., *Endocrinology* 137 (5):2167-2170 (1996) and Turnbull, A. V., et al., *Eur. J. Pharm.* 303:213-216 (1996)), urotensin I (Lederis, K., et al. *Science* 218:162-164 (1982)) and sauvagine (Montecucchi, P. C., et al., *Int. J. Pep. Prot. Res.* 16:191-199 (1980)).

CRF has been shown to have a peripheral, non-endocrine function mediated biological activity as a potent inhibitor of edema and inflammation (Wei, E. T. et al., *Ciba Foundation Symposium* 172:258-276 (1993)). This has been confirmed in a series of experiments in which systemic administration of CRF has been shown to inhibit vascular leakage of plasma constituents and associated tissue swelling in response to injury or inflammatory mediators (Wei, E. T. et al., *European J. of Pharm.* 140:63-67 (1987), Serda, S. M. et al., *Pharm. Res.* 26:85-91 (1992) and Wei, E. T. et al., *Regulatory Peptides* 33:93-104 (1991)).

In certain embodiments of the methods described herein the CRF is synthetic, e.g. corticorelin acetate. In certain embodiments, the CRF used is XERECEPT™. In certain embodiments of the methods described herein, derivatives, analogs and conjugates of CRF can be used. An example of a conjugate of CRF is PEG-conjugated CRF (CRF-PEG), described in U.S. Application Ser. No. 60/931,786, incorporated by reference herein.

In some embodiments, the CRF conjugates are administered to a human subject as a method of treating or managing cancers. CRF conjugates have an improved pharmacokinetic profile as compared to unmodified CRF. CRF conjugates may show an improvement in one or more parameters of the pharmacokinetic profile, including AUC, $C_{max}$, clearance (CL), half-life, and bioavailability as compared to unmodified CRF.

In certain embodiments, CRF is administered in the form of a pharmaceutical acceptable salt. As used herein and unless otherwise indicated, the term "pharmaceutically acceptable salt" includes, but is not limited to, salts of acidic or basic groups that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonase, salicylate, stearate, succinate, sulfate, tannate, tartrate, teoclate, triethiodide and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts. In a specific embodiment, the pharmaceutical acceptable salt of CRF is corticorelin acetate.

In certain embodiments, CRF conjugates include CRF with an unmodified amino acid sequence, wherein one or more residues are covalently bound to polyethylene glycol. CRF may be modified by covalently binding a polyethylene glycol polymer through one or more of its 41-amino acids including, but not limited to lysine, histidine, arginine, aspartic acid, glutamic acid, serine, as well as the N-terminal α-amino and C-terminal carboxylate groups of the protein. CRF conjugates also include cysteine added variants of CRF, where one or more cysteine residues have been inserted into one of the CRF amino acid sequences, or substituted for one or more residues of one of the CRF sequences. As used herein, the term "cysteine added variant of CRF" refers to CRF that has been modified by the insertion of one or more cysteine residues into the unmodified CRF sequence, or the substitution of one or more of the amino acid residues in the CRF polypeptide sequence, for cysteine residues. The conjugated cysteine added variants of CRF, include CRF sequences with cysteine residues added at the N-terminus, the C-terminus, or both the N-terminus and C-terminus of one of the amino acid sequences. Polyethylene glycol polymer units can be linear or branched. The CRF-PEG conjugate may be delivered intravenously or subcutaneously via injection.

There are a number of analogs of CRF known to the art. U.S. Pat. No. 4,415,558, issued Nov. 15, 1983, discloses the synthesis of sheep CRF, analogs, and isolation of the oCRF from ovine hypothalamic extracts. The synthetic OCRF was found to lower blood pressure.

A generally similar peptide, sauvagine, was described in Melchiorri and Negri, "Action of sauvagine on the mesenteric vascular bed of the dog," Regulatory Peptides 2:1-13 (1981). Sauvagine is a 40 amino acid peptide and has been reported to have biological activity in lowering blood pressure in mammals and stimulating the secretion of ACTH and β-endorphin.

U.S. Pat. No. 4,528,189, issued Jul. 9, 1985, and U.S. Pat. No. 4,533,654, issued Aug. 6, 1985, disclose peptides similar to the rat and sheep CRF and analogs thereof, and found this white sucker and carp urotensin respectively to stimulate ACTH and to lower blood sugar.

Ling et al., "Isolation and characterization of caprine corticotropin-releasing factor," Biochem Biophys Res Commun. 122:1218-1224 (1984), disclose the structure of goat CRF, which is the same as that for sheep CRF. Esch et al., "Isolation and characterization of the bovine hypothalamic corticotropin-releasing factor," Biochem Biophys Res Commun. 122: 899-905 (1984), disclose the structure of bovine CRF which differs from sheep and goat CRF only by one amino acid residue (number 33, which is asparagine, rather than the number 33 serine of goat and sheep CRF). Porcine CRF has been isolated and characterized by Patthy et al., "Isolation and amion acid sequence of corticotrophin-releasing factor from pig hypothalami," Proc Natl Acad Sci USA 82:8762-8766 (1985). Porcine CRF shares a common amino acid sequence (residues 1-39) with rat/human CRF and differs from these only in position 40 and 41. Residue 40 can be either asparagine or isoleucine and residue 41 is phenylalanine-amide.

By "CRF" is meant herein mammalian corticotropin-releasing factor, including that isolatable from rat, human, cow, goat, pig, or sheep. Analogs of CRF include sauvagine, carp urotensin, and sucker urotensin (all of which have been isolated from lower vertebrates), and those synthetic peptide structure analogous to CRF and disclosed in U.S. Pat. Nos. 4,415,558, 4,489,163, 4,553,654, and 4,528,189, incorporated herein by reference.

6.2 Dosage and Administration

In one embodiment, the total daily dose of CRF that is administered to a patient to treat or manage cancer or to prevent tumor progression can range from 1 µg to 100 mg; 2 µg to 50 mg; 5 µg to 25 mg; 10 µg to 20 mg; 50 µg to 10 mg; 100 µg to 5 mg; 500 µg to 3 mg; 1 mg to 2 mg. In another embodiment, the dose of CRF contained in pharmaceutical formulation can range from 1 µg to 10 mg. In certain embodiments, the dose of CRF can range from 0.1 mg to 5 mg, or 0.3 mg to 2 mg. In certain embodiments, the dose of CRF can be about 0.3 mg, about 0.5 mg, about 1 mg, about 2.5 mg, about 4 mg or about 5 mg. In certain embodiments, the total daily dose of CRF can be 4 mg to 10 mg. For example, the total daily dose of CRF can be about 1 mg, about 2 mg, about 2.5 mg, about 3.0 mg, about 4 mg, about 6 mg, about 8 mg, about 10 mg, about 12 mg, 15 mg, about 17 mg, or about 20 mg. In one embodiments, CRF is administered by subcutaneous injection in an amount of 0.1 µg/kg to 1000 µg/kg. CRF can be administered subcutaneously, intravenously, topically, intradermally, transdermally, intranasally, or via pulmonary in an amount of 1 µg/kg to 500 µg/kg, 2 µg/kg to 100 µg/kg, 2 µg/kg to 80 µg/kg, 4 µg/kg to 40 µg/kg, or 5 µg/kg to 20 µg/kg. For example, CRF can be administered in 3 µg/kg, 10 µg/kg, 30 µg/kg, 60 µg/kg, 100 µg/kg and 300 µg/kg doses. In another embodiment, CRF is administered by intravenous infusion at a rate of 0.1 µg/kg/h to 100 µg/kg/h. For example, CRF can be administered intravenously at a rate of 1 µg/kg/h to 100 µg/kg/h, or 2 µg/kg/h to 80 µg/kg/h, or 2 µg/kg/h to 50 µg/kg/h, or 4 µg/kg/h to 40 µg/kg/h, or 5 µg/kg/h to 20 µg/kg/h.

The administered dose of CRF can be delivered as a single dose (e.g. a single bolus injection) or over a 24-hour period (e.g., continuous infusion over time or divided bolus doses over time) and is repeated until the patient experiences stable disease or regression, or until the patient experiences disease progression or unacceptable toxicity. For example, stable disease for solid tumors generally means that the perpendicular diameter of measurable lesions has not increased by 25% or more from the last measurement. See e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

In other embodiments, CRF is administered in combination with another drug ("second active agent") or another therapy for treating or managing cancer. Second active agents include small molecules and large molecules (e.g., proteins and antibodies), examples of which are provided herein, as well as stem cells or cord blood. Methods, or therapies, that can be used in combination with the administration of CRF include, but are not limited to, surgery, immunotherapy, biological therapy, radiation therapy and other non-drug based therapies presently used to treat or manage cancer. Various dosing regimens for administration of CRF alone and/or in combination therapy are discussed herein.

The terms "co-administration" and "in combination with" include the administration of two therapeutic agents (for example, CRF and another anti-cancer agent or second agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

Also provided are pharmaceutical compositions (e.g., single unit dosage forms) that can be used in methods disclosed herein. Particular pharmaceutical compositions comprise CRF and a second active agent.

In one embodiment, CRF conjugates can be used to treat cancer by administering to a patient in need thereof a therapeutically acceptable amount of a CRF conjugate.

In another embodiment, a method of treating cancer comprises administering to a patient in need thereof a pharmaceutical composition comprising CRF chemically modified with polyethylene glycol and a pharmaceutically acceptable diluent, adjuvant or carrier.

As used herein, the term "pharmaceutically acceptable" when used in reference to the formulations of the present disclosure denotes that a formulation does not result in an unacceptable level of irritation in the subject to whom the formulation is administered by any known administration regimen. What constitutes an unacceptable level of irritation will be readily determinable by those of ordinary skill in the art and will take into account erythema and eschar formation as well as the degree of edema associated with administration of the formulation.

6.3 Dosing Regimens

In any of the above described methods, CRF can be administered once a day or multiple times a day. For example, the dosages of CRF can be administered every hour, every two hours, every three hours, every four hours, every six hours, every eight hours, every 12 hours or every 24 hours. Alternatively, CRF can be administered once every two, three, four, five or six days. In certain embodiments CRF can be administered once a week, once every two, three or four weeks or once a month.

Additionally, CRF has been shown to be well tolerated when administered over long periods of time. Therefore, a patient who is administered CRF can be placed on a dosing regimen wherein the patient receives, e.g., corticorelin acetate over an extended period of time. In certain embodiments, the patient can receive administrations of CRF over a period of 3 days, 4, days, 5 days, 1 week, 2 weeks, 3 weeks, or 4 weeks or more. In still other embodiments a patient can receive CRF over a period of 1 month, 2 months, 3 months, 4 months, 5 months, 6 months or more. In some instances the patient can receive CRF over a period of 1 year or longer.

In one embodiment, for any of the methods described above, the total daily dose of CRF can range from about 0.01 mg to about 100 mg. In another embodiment, the total daily dose of CRF contained in pharmaceutical formulation can range from 1 µg to 10 mg. In certain embodiments, the dose of CRF can range from 0.1 mg to 5 mg, or 0.3 mg to 2 mg. In certain embodiments, the dose of the CRF can be about 0.3 mg, about 0.5 mg, about 1 mg, about 2 mg, about 4 mg or about 5 mg. In certain embodiments, the total daily dose of CRF can be 4 mg to 10 mg. For example, the total daily dose of CRF can be about 1 mg, about 2 mg, about 2.5, about 3 mg, about 4 mg, about 6 mg, about 8 mg, about 10 mg, about 12 mg, 15 mg, about 17 mg, or about 20 mg. CRF can be administered once a day or multiple times a day until the desired daily dose of CRF is reached. For example, 0.5 mg or 1.0 mg of CRF can be administered 2 times a day to achieve a total daily dose of 1 mg or 2 mg of CRF. Alternatively, 0.5 mg or 1.0 mg of CRF can be administered 4 times a day to achieve a total daily dose of 2 mg or 4 mg of CRF.

In certain embodiments, CRF is administered twice day. In certain embodiments, CRF is administered twice day in a total daily dose of 1 mg.

CRF can also be administered in conjunction with an additional anti-cancer therapy. Anti-cancer treatments include radiotherapy, chemotherapy, photodynamic therapy, surgery or other immunotherapy. Chemotherapy can include the administration of anti-neoplastic, anti-proliferative, anti-miotic agents such as those discussed in Section 6.2.

In another preferred embodiment, CRF is administered to a patient receiving radiation therapy for treatment of cancer. For radiation treatment, the radiation can be gamma rays or X-rays. The methods encompass administering CRF to a patient receiving radiation therapy, such as external-beam radiation therapy, interstitial implantation of radioisotopes (1-125, palladium, or iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J.B. Lippencott Company, Philadelphia.

When CRF is administered with anti-cancer agents, the CRF and the anti-cancer agent can be administered sequentially or simultaneously. If administered sequentially, the order of administration is flexible.

In certain embodiments, CRF described herein is administered by subcutaneous injection in an amount of 0.1 µg/kg to 1000 µg/kg. CRF can be administered subcutaneously in an amount of 1 µg/kg to 500 µg/kg, 2 µg/kg to 100 µg/kg, 2 µg/kg to 80 µg/kg, 4 µg/kg to 40 lag/kg, or 5 µg/kg to 20 µg/kg. For example, CRF can be administered in 10 µg/kg, 30 µg/kg, 60 µg/kg, 100 µg/kg and 300 µg/kg doses.

In other embodiments, CRF described herein can be administered by subcutaneous injection in an amount of 1 µg to 100 mg. CRF can be administered subcutaneously in an amount of 1 µg to 80 mg, 10 µg to 50 mg, 100 µg to 40 mg, 300 µg to 10 mg, 600 µg to 1 mg, and 800 µg to 1 mg. For example, CRF can be administered subcutaneously in 100 µg, 300 µg, 600 µg, 1 mg, 2 mg, 2.5 mg, 3 mg, 4 mg and 5 mg doses.

CRF administered subcutaneously can be administered once a day or multiple times a day. For example, the dosages of CRF administered subcutaneously can be administered every hour, every two hours, every three hours, every four hours, every six hours, every eight hours or every 12 hours. Alternatively, CRF can be administered once every two, three, four, five or six days. In certain embodiments CRF can be administered once a week, once every two, three or four weeks or once a month. Dosages of CRF that are administered once a week or longer can be administered in the form of a depot. For example, the present disclosure includes methods of managing or treating tumors comprising administering to a patient, preferably a human, in need thereof a therapeutically effective amount of, e.g., corticorelin acetate by subcutaneous injection.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder or enhances the therapeutic efficacy of another therapeutic agent.

Corticorelin can also be administered by other parenternal routes of administration such as, but not limited to, intradermal and intramuscular injections, and intravenous or intraosseous infusions. For example, CRF can be administered by intravenous infusion at a rate of 0.1 µg/kg/h to 100 µg/kg/h. For example, CRF can be administered intravenously at a rate of 1 µg/kg/h to 100 µg/kg/h, or 2 µg/kg/h to 80 µg/kg/h, or 2 µg/kg/h to 50 µg/kg/h, or 4 µg/kg/h to 40 µg/kg/h, or 5 µg/kg/h to 20 µg/kg/h.

In other embodiments CRF can be administered intravenously in an amount of 1 µg/kg to 1000 µg/kg. For example CRF can be administered intravenously in an amount of 1 µg/kg to 100 µg/kg, or 2 µg/kg to 80 µg/kg, or 2 µg/kg to 50 µg/kg, or 4 µg/kg to 40 µg/kg, or 5 µg/kg to 20 µg/kg. For example, CRF can be administered in 0.5 µg/kg to 1 µg/kg, or 2 µg/kg to 8 µg/kg, or 4 µg/kg to 8 µg/kg, or 5 µg/kg doses.

CRF can be administered intravenously over a period of an hour or less than an hour. In certain embodiments CRF can be administered intravenously over a period of one hour or more. For example, the dosages of CRF administered intravenously, discussed above can be administered over a period of 10 min., 30 min., 45 min., one hour, two hours, four hours, eight hours, 12 hours, 24 hours, 48 hours or 72 hours.

In certain embodiment the dosing regimens comprises administering CRF with a steroid. The CRF and the steroid can be administered sequentially or simultaneously. If administered sequentially, the order of administration is flexible. In a specific embodiment, CRF is administered subcutaneously. In another specific embodiment, the steroid, such as dexamethasone is administered orally.

6.4 Second Active Agents

In the methods and compositions provided herein, CRF can be used with or combined with other pharmacologically active compounds ("second active agents"). It is believed that certain combinations work synergistically in the treatment of particular types of cancers. CRF can also work to alleviate adverse effects associated with certain second active agents, and some second active agents can be used to alleviate adverse effects associated with CRF.

One or more second active ingredients or agents can be used in the methods and compositions provided herein together with CRF. Second active agents can be large molecules (e.g., proteins) or small molecules (e.g., synthetic inorganic, organometallic or organic molecules).

Examples of large molecule active agents include, but are not limited to, hematopoietic growth factors, cytokines, and monoclonal and polyclonal antibodies, particularly therapeutic antibodies to cancer antigens. Typical large molecule active agents are biological molecules, such as naturally occurring or artificially made proteins. Proteins that are particularly useful in the methods and compositions provided herein include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPOGEN® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Also provided for use in combination with CRF are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with CRF include monoclonal and polyclonal antibodies. Examples of antibodies include, but are not limited to, trastuzumab (HERCEPTIN®), rituximab (RITUXAN®), bevacizumab (AVASTINT™), pertuzumab (OMNITARG™), tositumomab (BEXXAR®), edrecolomab (PANOREX®), and G250. CRF can also be combined with or used in combination with, anti-TNF-α antibodies.

Large molecule active agents may be administered in the form of anti-cancer vaccines. For example, vaccines that secrete or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Second active agents that are small molecules can also be used to alleviate adverse effects associated with the administration of CRF. However, like some large molecules, many are believed to be capable of providing a synergistic effect when administered with (e.g., before, after or simultaneously) CRF. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin (VISUDYN™); verteporfin photodynamic therapy; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; amsacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin (ELOXATN™); oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, rituximab, oblimersen (GENASENS®), remicade, docetaxel (TAXOTERE®), celecoxib, melphalan, dexamethasone (DECADRON®), steroids, gemcitabine, cisplatinum, temozolomide, etoposide, cyclophosphamide, temozolomide (TEMODAR®), carboplatin, procarbazine, gliadel, tamoxifen, topotecan, methotrexate, ARISA®, taxol, taxotere, fluorouracil, 5-fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin (PARAPLATI10, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel (TAXOL®), ganciclovir, adriamycin, estramustine sodium phosphate (EMCYT®), sulindac, and etoposide.

In certain embodiments, the second active agent is etoposide, daunomycin, actinomycin D, mitomycin C, cisplatin, carboplatin, premetrexed, methotrexate, Ara-C, 5-Fu, wortmannin, gemcitabin, geldanamycin or a combination thereof.

6.5 Combination Therapy with a Second Active Agent

In certain embodiments, the methods provided herein comprise administering CRF in combination with one or more second active agents, and optionally in combination with radiation therapy or surgery. The administration of CRF and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., *Physicians' Desk Reference,* 1755-1760 (56$^{th}$ ed., 2002).

In one embodiment, the second active agent is administered intravenously or subcutaneously and once or twice daily in an amount of from about 1 to about 1,000 mg, from about 5 to about 500 mg, from about 10 to about 375 mg, or from about 50 to about 200 mg. In certain embodiments, the second active agent is rituximab, oblimersen (GENASENSE®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof. In certain embodiments, the second active agent is etoposide, daunomycin, actinomycin D, mitomycin C, cisplatin, carboplatin, premetrexed, methotrexate, Ara-C, 5-Fu, wortmannin, geldanamycin, gemcitabin, or a combination thereof.

In another embodiment, provided herein are methods of treating or managing hematologic malignancies, which comprise administering CRF in conjunction with (e.g., before, during or after) conventional therapy including, but not limited to, surgery, immunotherapy, biological therapy, radiation therapy, or other non-drug based therapy presently used to treat or manage cancer. Without being limited by theory, it is believed that CRF may provide additive or synergistic effects when given concurrently with conventional therapy.

In certain embodiments, the second active agent is co-administered with CRF or administered with 1-50 hours delay. In certain embodiments, CRF is administered first followed by administration with the second active agent with 1-50 hours delay. In certain embodiments, the second active agent is administered first followed by administration of CRF with 1-50 hours delay. In certain embodiments, the delay is 24 hours. In certain embodiments, the CFT is pegylated CFT.

In one embodiment, CRF is administered in an amount from 1 µg/kg to 1,000 µg/kg, from 1 µg/kg to 100 µg/kg, from 2 µg/kg to 80 µg/kg, from 2 µg/kg to 50 µg/kg, from 4 µg/kg to 40 µg/kg, or from 5 µg/kg to 20 µg/kg alone or in combination with a second active agent disclosed herein, prior to, during, or after the use of conventional therapy.

In certain embodiments, the second active agent is temozolomide. In certain embodiments, the CFT is pegylated CFT and the second active agent is temozolomide.

In certain embodiments, the daily dose of temozolomide is from about 1 to about 5,000 mg, from about 1 to about 1,000 mg, or from about 10 to 500 mg per day. In certain embodiments, the daily dose of temozolomide is about 10 mg, about 25 mg, about 50 mg, about 75 mg, about 83 mg, about 90 mg, about 98 mg, about 105 mg, about 112 mg, about 120 mg, about 128 mg, about 135 mg, about 143 mg, about 150 mg, about 158 mg, about 165 mg, about 173 mg, about 180 mg, about 188 mg, about 195 mg, about 200 mg, about 210 mg, about 220 mg, about 225 mg, about 240 mg, about 255 mg, about 260 mg, about 270 mg, about 280 mg, about 285 mg, about 300 mg, about 315 mg, about 320 mg, about 330 mg, about 340 mg, about 345 mg, about 360 mg, about 375 mg, about 380 mg, about 400 mg, about 420 mg, about 440 mg, about 460 mg, about 480 mg, or about 500 mg.

In certain embodiments, temozolomide is administered in an amount ranging from about 10 to about 500 mg/m$^2$/day, from about 50 to about 250 mg/m$^2$/day, or about 75 to about 200 mg/m$^2$/day. In certain embodiments, temozolomide is administered in an amount of about 10 mg/m$^2$/day, about 20 mg/m$^2$/day, about 30 mg/m$^2$/day, about 40 mg/m$^2$/day, about 50 mg/m$^2$/day, about 75 mg/m$^2$/day, about 100 mg/m$^2$/day, about 125 mg/m$^2$/day, about 150 mg/m$^2$/day, about 175 mg/m$^2$/day, or 200 about mg/m$^2$/day.

The administered dose can also be expressed in units other than as mg/m$^2$/day. For example, doses for parenteral administration can be expressed as mg/kg/day. One of ordinary skill in the art would readily know how to convert doses from mg/m$^2$/day to mg/kg/day given either the height or weight of a subject or both (see, www.fda.gov/cder/cancer/animalframe.htm).

In certain embodiments, temozolomide is cyclically administered. In certain embodiments, temozolomide is administered daily in a single or divided doses for five days, one week, two weeks, three weeks, four weeks, five weeks, six weeks, eight weeks, ten weeks, fifteen weeks, or twenty weeks, followed by a rest period of about 1 day to about ten weeks. In certain embodiments, temozolomide is administered daily in a single or divided doses for five days, one week, two weeks, three weeks, four weeks, five weeks, six weeks, or eight weeks with a rest period of 1, 3, 5, 7, 9, 12, 14, 16, 18, 20, 22, 23, 24, 25, 26, 28, 29 or 30 days. In certain embodiments, the rest period is 7 days. In certain embodiments, the rest period is 14 days. In certain embodiments, the rest period is 23 days. In certain embodiments, the rest period is a period that is sufficient for bone marrow recovery. In certain embodiments, the rest period is a period that is sufficient for neutrophil recovery. In certain embodiments, the rest period is a period that is sufficient for platelet recovery. The frequency, number, and length of dosing cycles can be increased or decreased.

In certain embodiments, temozolomide is administered daily for four weeks, followed by six cycles of maintenance treatment. In certain embodiments, temozolomide in cycle 1 is administered once daily for five days, followed by a rest period of twenty-three (23) days. In certain embodiments, temozolomide in each of cycles 2 to 6 is administered once daily for five days, followed by a rest period that is sufficient for neutrophil and platelet recovery. In certain embodiments, each of cycles 2 to 6 starts when absolute neutrophil count (ANC) exceeds 1.5×10$^9$/L and the platelet count exceeds 100×10$^9$/L. In certain embodiments, the administration of temozolomide during cycles 1 to 6 may be discontinued if ANC is below 1×10$^9$/L or platelet count is below 50×10$^9$/L. The dosage in each cycle can be increased or decreased.

In certain embodiments, temozolomide is administered orally at 75 mg/m$^2$ daily for 42 days concomitant with 400 focal radiotherapy (60 Gy administered in 30 fractions) followed by maintenance treatment. Four weeks after completing the temozolomide and radiotherapy, temozolomide is administered for an additional 6 cycles of maintenance treatment. In cycle 1, temozolomide is administered at 150 mg/m$^2$ once daily for 5 days followed by 23 days without treatment. At the start of cycle 2, the dose is escalated to 200 mg/m$^2$, if the common toxicity criteria (CTC) non-hematologic toxicity for cycle 1 is no greater than Grade 2 (except for alopecia, nausea, and vomiting), absolute neutrophil count (ANC) is no less than 1.5×10$^9$/L, and the platelet count is no less than 100×10$^9$/L. The dose remains at 200 mg/m$^2$ per day for the first 5 days of each subsequent cycle except if toxicity occurs. If the dose was not escalated at cycle 2, escalation should not be done in subsequent cycles.

In certain embodiments, the daily dose of temozolomide is adjusted according to neutrophil and platelet counts.

In another embodiment, the methods provided herein comprise: a) administering to a patient in need thereof, a dose of about 1 mg to 20 mg of CRF and b) administering a therapeutically effective amount of a supportive care agent.

The term "the supportive care agent" refers to any substance that treats, prevents or manages an adverse effect from CRF treatment.

The supportive care agent is any substance that treats, prevents or manages an adverse effect from CRF treatment and is administered according to the appropriate dosing regimen for that substance. For example, different supportive care agents for treating nausea have different dosing regimen. While some are administered prophylactically, others are co-administered with CRF while still others are administered after the administration of CRF. Illustrative examples of supportive care agents their doses and dosing regimens are found in The Physician's Desk Reference.

6.6 Pharmaceutical Compositions and Dosage Forms

The methods provided herein use pharmaceutical compositions containing CRF and pharmaceutically acceptable carriers, such as diluents or adjuvants, or in combination with other active ingredient, such as another anti-cancer agent. In clinical practice CRF may be administered by any conventional route, including, but not limited to, orally, parenterally, rectally or by inhalation (e.g. in the form of aerosols). In one embodiment, CRF is administered by a subcutaneous injection. In another embodiment, CRF is administered by IV injection.

In one embodiment, the methods provided herein use pharmaceutical compositions containing corticorelin acetate as the active ingredient to be administered in accordance with the methods described herein. The corticorelin acetate may be formulated with a pharmaceutically acceptable carrier. The pharmaceutical formulations of the present disclosure can take the form of solutions, suspensions, emulsions that include corticorelin acetate, and a pharmaceutically acceptable diluent, adjuvant or carrier. In certain embodiments, the pharmaceutical formulations of the present disclosure are formulated for subcutaneous bolus injection.

In another embodiment, the methods provided herein use pharmaceutical compositions containing corticorelin acetate formulated for subcutaneous injection provided for treatment of tumors. In certain embodiments, administration of subcutaneous formulations of corticorelin acetate can result in less frequent administration of corticorelin acetate than administration of other non-subcutaneous formulations of corticorelin acetate. Less frequent administration of corticorelin acetate can result in greater patient compliance. Additionally, in other embodiments, administration of subcutaneous formulations of corticorelin acetate can result in fewer side-effects associated with administration of non-subcutaneous formulations of corticorelin acetate.

In certain embodiments, provided herein are methods of preventing tumor progression in a patient by administering pharmaceutical compositions containing a CRF conjugate as the active ingredient. The CRF conjugate may be formulated with a pharmaceutically acceptable carrier. Due to the increased half-life of the CRF conjugate, the pharmaceutical compositions may contain a lower dose of CRF. The pharmaceutical formulations of the present disclosure can take the form of solutions, suspensions, emulsions that include a CRF conjugate, such as CRF chemically modified with polyethylene glycol, and a pharmaceutically acceptable diluent, adjuvant or carrier, depending on the route of administration.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

Pharmaceutical compositions can be used in the preparation of individual, single unit dosage forms. Pharmaceutical compositions and dosage forms comprise CRF and one or more excipients.

Pharmaceutical compositions and dosage forms can also comprise one or more additional active ingredients. Examples of optional second, or additional, active ingredients are disclosed herein.

In certain embodiments, a composition provided herein is a pharmaceutical composition or a single unit dosage form. Pharmaceutical compositions and single unit dosage forms provided herein comprise a prophylactically or therapeutically effective amount of CRF, and typically one or more pharmaceutically acceptable carriers or excipients. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, powders and the like. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such as an animal subject, or a mammalian subject, and such as a human subject.

A pharmaceutical composition provided herein is formulated to be compatible with its intended route of administration. Examples of routes of administration include, but are not limited to, parenteral, e.g., intravenous, intradermal, subcutaneous, intramuscular, subcutaneous, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of disease may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., *Remington's Pharmaceutical Sciences,* 20th ed., Mack Publishing, Easton Pa. (2000).

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of CRF may be formulated to deliver a therapeutic dose of corticorelin acetate. In certain embodiments, the dose of corticorelin acetate contained in a pharmaceutical formulation can range from 1 mg to 20 mg. In another embodiment, the dose of CRF contained in a pharmaceutical formulation can range from 1 µg to 10 mg. In certain embodiments, the dose of CRF can range from 0.1 mg to 5 mg, or 0.3 mg to 2 mg. In certain embodiments, the dose of CRF can be about 0.3 mg, about 0.5 mg, about 1 mg, about 2.5 mg, about 4 mg or about 5 mg.

In certain embodiments, the total daily dose of CRF can be 4 mg to 10 mg. For example, the total daily dose of CRF can be about 1 mg, about 2 mg, about 4 mg, about 6 mg, about 8 mg, about 10 mg, about 12 mg, 15 mg, about 17 mg, or about 20 mg. The doses can be determined by methods known in the art and the pharmaceutical formulations of the present disclosure can be administered alone or in combination to prevent tumor progression.

6.6.1 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of active ingredients. See, e.g., U.S. Pat. No. 5,134,127, which is incorporated herein by reference.

6.6.2 Topical, Transdermal, and Mucosal Dosage Forms

In certain embodiments, provided herein are transdermal, topical, and mucosal dosage forms. Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 20th ed., Mack Publishing, Easton Pa. (2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 20th ed., Mack Publishing, Easton Pa. (2000).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

6.7 Methods of Monitoring Tumors

In certain embodiments, tumors and tumor progression can be monitored/assessed using standard techniques known to one of skill in the art. In certain embodiments of the therapeutically effective regimens of the disclosure, the regimens result in a stabilization of the tumor size/volume or a reduction in tumor progression. In one embodiment, the subject undergoing the regimen is monitored to determine whether the regimen has resulted in a stabilization of the tumor size/volume or reduction in tumor progression. In some embodiments, tumor progression is monitored before, during and after onset of treatment with CRF.

In certain embodiments, tumor progression is assessed in a subject or a sample from a subject at least 1, 2, 4, 6, 8, 10, 12, 14, 15, 16, 18, 20, or 30, 60, 90 days 6 months, 9 months, 12 months, >12 months after the subject begins receiving the regimen. In certain embodiments, tumor progression is assessed after a subject has received a number of doses of a therapy (e.g., after 1, 2, 5, 10, 20, 30 or more doses of a therapy). In other embodiments, tumor progression is assessed after 2 weeks, 1 month, 2 months, 1 year, 2 years, 3 years, 4 years or more after receiving one or more therapies.

Tumor progression can be measured to assess the efficacy of the regimen. In one embodiment, the reference sample is a sample from the subject undergoing therapy, at an earlier time point (e.g., prior to receiving the regimen as a baseline reference sample, or at an earlier time point while receiving the therapy). In this embodiment, the therapy desirably results in a decrease in tumor progression in the test sample as compared with the reference sample. In another embodiment, the reference sample is obtained from a healthy, subject who has no detectable cancer, or from a patient that is in remission for the same type of cancer.

Tumor progression can be monitored/assessed using standard techniques known to one of skill in the art. A number of known methods can be used to assess the bulk size of the tumor. Non-limiting examples of such methods include imaging methods (e.g., computed tomography (CT), magnetic resonance imaging (MRI), positron emission tomography (PET) scans, palpitation, direct measurement (e.g. with a ruler), ultrasound, X-ray imaging, mammography, bone scans and radioisotope imaging), visual methods (e.g., colonoscopy, bronchoscopy, and endoscopy), physical examination (e.g., prostate examination, breast examination, lymph nodes examination, abdominal examination, general palpation), blood tests (e.g., prostate specific antigen (PSA) test, carcinoembryonic antigen (CEA) test, cancer antigen (CA)-125 test, alpha-fetoprotein (AFP)), bone marrow analyses (e.g., in cases of hematological malignancies), histopathology, cytology and flow cytometry.

In some embodiments, the bulk tumor size can be measured by assessments based on the size of tumor lesions determined from imaging methods. In specific embodiments, the assessments are performed in accordance with the Response Evaluation Criteria In Solid Tumors (RECIST) Guidelines, which are set forth in Therasse, et al. (J. Nat. Canc. Inst. 2000, 92(3), 205-216). For instance, in specific embodiments, lesions in the subject that are representative of bulk tumor size are selected so that they are at least 20 mm in their longest diameter at baseline (prior to treatment) when conventional imaging techniques are used (e.g., conventional CT scan, MRI or x-ray) and lesions that are at least 10 mm in their longest diameter at baseline should be selected when spiral CT scanning is used.

7. EXAMPLES

7.1 Pre-Clinical Studies

This example demonstrates that brain tumor-bearing mice, that are administered a high dose of CRF, i.e. 100 µg/kg s.c. twice daily, survive longer than untreated control mice or mice that receive treatment with a chemotherapeutic agent or that are administered dexamethasone.

The results were obtained with SCID mice bearing brain tumors produced by injection with the human glioblastoma cell line U87 Flue. The U87 Flue cell line was created by stably transducing U87 cells with a lentiviral construct containing the luc gene.

All brain tumor-bearing mice that were administered a high dose of CRF survived the entire 80-day study period and appeared healthy throughout. Similarly, mice that received a low dose of CRF survived longer than mice that were left untreated or that were administered dexamethasone or chemotherapeutic agents (BiCNU or TMZ). At the end of the 80-day study period, 60% of the mice that were treated with a low dose of CRF were still alive, while all mice that had received dexamethasone treatment had died. All mice, that had not received any treatment, and most mice, that were administered chemotherapeutic agents, had to be euthanized before the end of the 80-day study period. For example, only 40% of the TMZ-treated mice were still alive at the end of the 80-day study period.

Mice, that were administered a low dose of CRF, had a mean survival time between mice, that were administered a high dose of CRF, and mice that had received no treatment or were administered dexamethasone.

The brain tumors in mice, that were administered a high dose of CRF, did not progress during the 80-day study period, and tumor size appeared to remain relatively constant based on luminescence imaging results. Similarly, the brain tumors in mice, that were administered a low dose of CRF, did not progress or progressed more slowly. In contrast, brain tumors of mice that received a high dose of dexamethasone continuously progressed over time.

Brain tumors in mice, that were administered BiCNU, also continued to grow, and the tumors did not appear to respond well to treatment with BiCNU. Brain tumors in all mice but one, that were administered TMZ, responded to the treatment. However, the tumors appeared to go through periods of expansion, which was in contrast to observations brain tumor-bearing mice treated with high doses of CRF, where tumor size remained relatively constant. The response to chemotherapy directly correlated with tumor growth detected by photon emission. TMZ-treated mice had a longer mean survival time than BiCNU-treated mice.

Similarly, mice, that were administered a high dose of CRF, did not show tumor progression based on photon emission and remained healthy throughout the 80-study period.

7.2 Combination Treatment

This example demonstrates the efficacy of administration of CRF with Applicants have also found that CRF, when used in combination with one or more agents. CRF may be administered in combination with another drug ("second active agent") or another therapy for treating or managing cancer. One such example of another drug or antoher therapy for treating or managing cancer is an angiogenesis inhibitor, such as bevacizumab (Avastin®) or sunitinib malate (Sutent®). In this example, CRF is adminstered with the angiogenesis inhibitor bevacizumab (Avastin®) to treat a variety of different tumor types. These studies demonstrate that the combination of CRF and bevacizumab (Avastin®) is more effective at treat cancer than either single treatment alone.

Figure 4B:
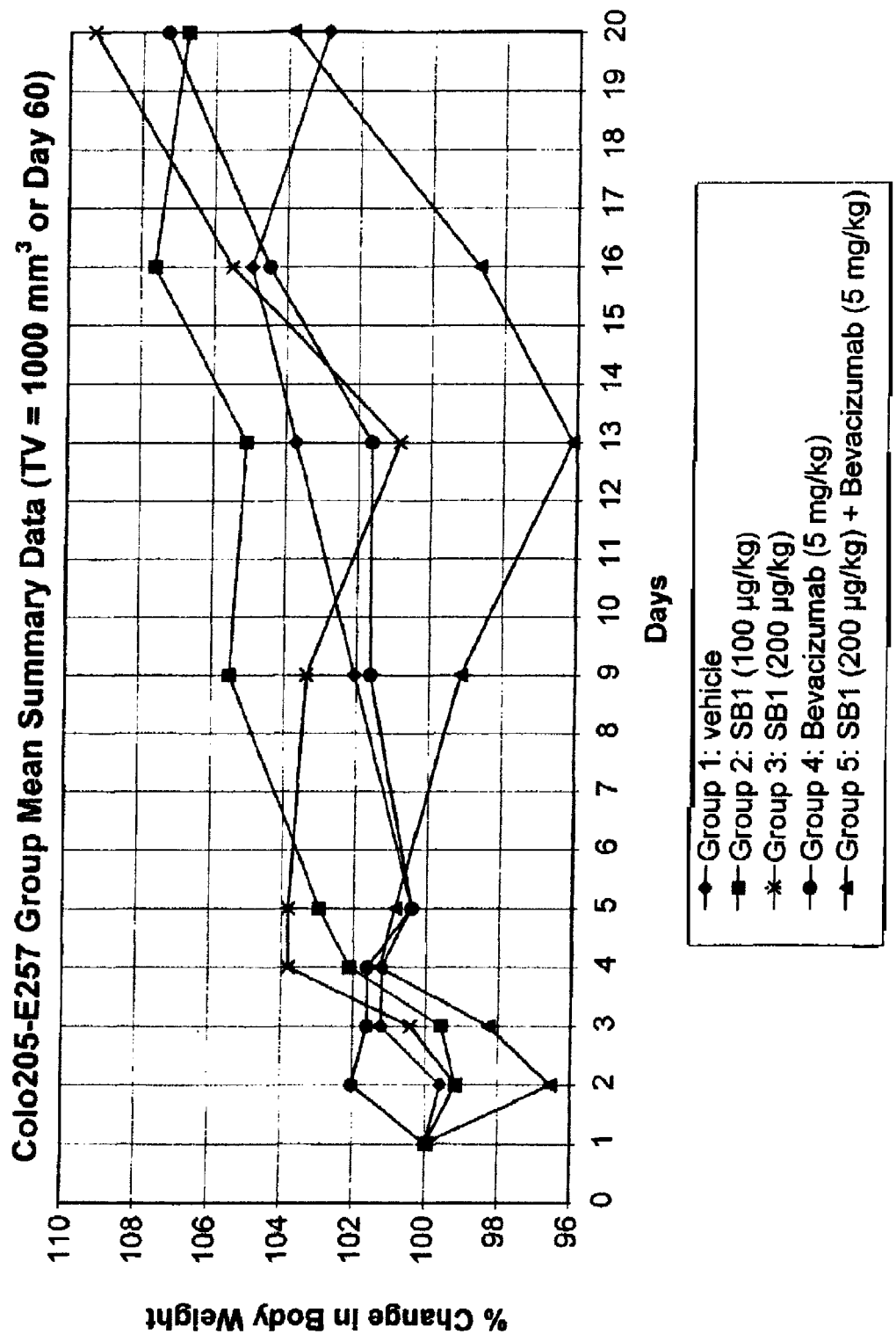
FIG. 4B shows a graph of the change in body weight over time in mice involved in a study analyzing the effect of administration of CRF, bevacizumab (Avastin®), or CRF and bevacizumab (Avastin®) on human colon tumor cell growth.
Figure 4C:
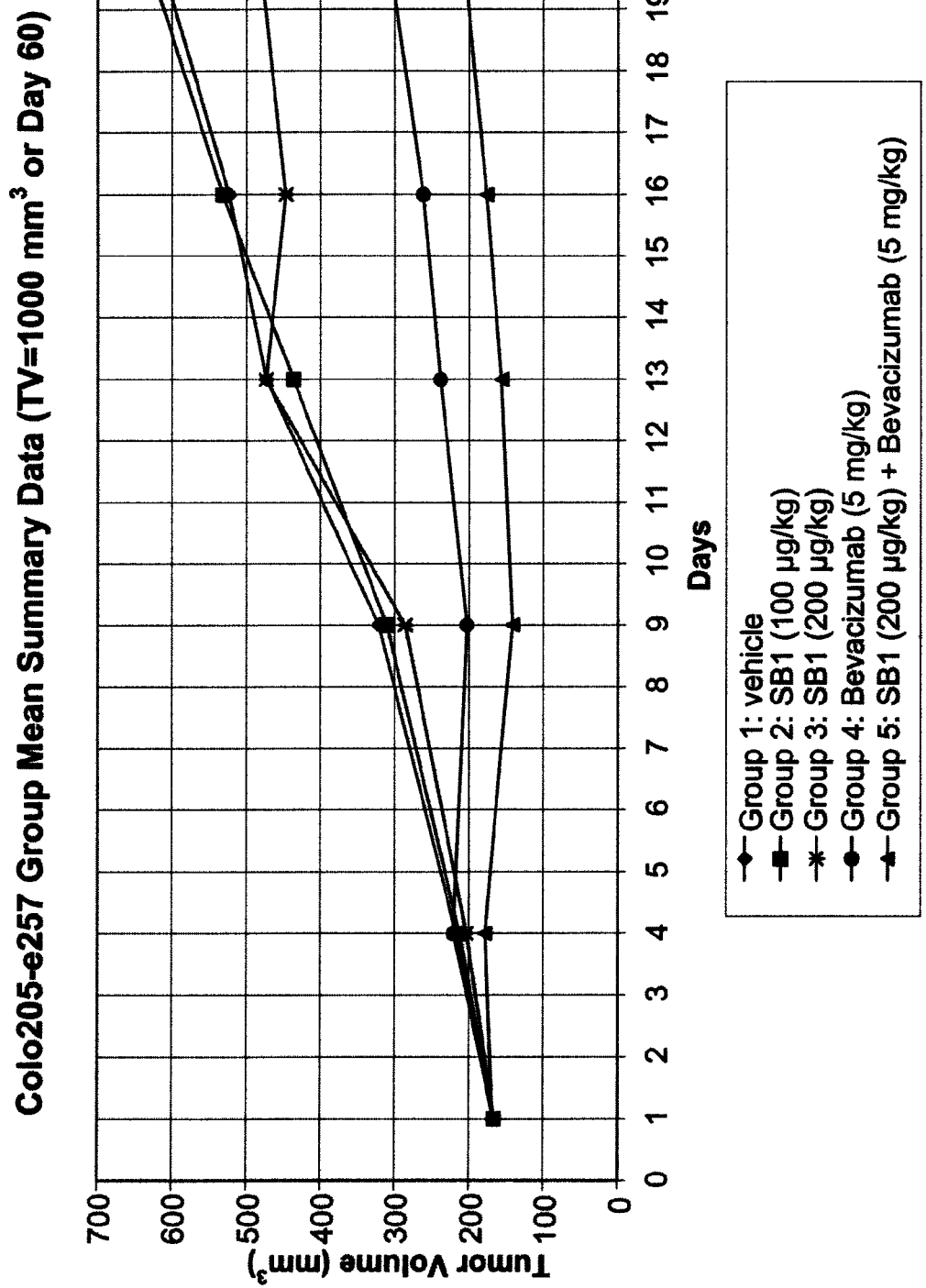
FIG. 4C shows a graph of the change in tumor volume over time in mice involved in a study analyzing the effect of administration of CRF, bevacizumab (Avastin®), or CRF and bevacizumab (Avastin®) on human colon tumor cell growth.

In one study, 8-12 week old female nu/nu mice were injected with $1 \times 10^6$ Colo205 human colon tumor cells subcutaneously. Once tumors developed and reached an average size of 100-150 mg, mice received administration of (1) saline (control) (twice daily, subcutaneous); (2) CRF (100 µg/kg) (twice daily, subcutaneous); (3) CRF (200 µg/kg) (twice daily, subcutaneous); (4) bevacizumab (Avastin®) (5 mg/kg) (twice weekly, intraperitoneal); or (5) CRF (200 µg/kg) (twice daily, subcutaneous) and bevacizumab (Avastin®) (5 mg/kg) (twice weekly, intraperitoneal) (FIG. 4A). Body weight and tumor volume were measured twice a week until the endpoint of the experiment, i.e., the earlier of either 60 days or a tumor volume of 1000 mm$^3$. Results indicate that a reduction in tumor volume in mice receiving single agents as compared to control, and the most reduction in tumor volume in mice receiving a combination of CRF and bevacizumab (Avastin®) (FIGS. 4B-4D). This study suggests that the effect of administering a combination of CRF and bevacizumab (Avastin®) on inhibiting the development or growth of a colon tumor and/or on the reduction of colon tumor size great than administering either CRF alone or bevacizumab (Avastin®) alone.

Figure 5B:
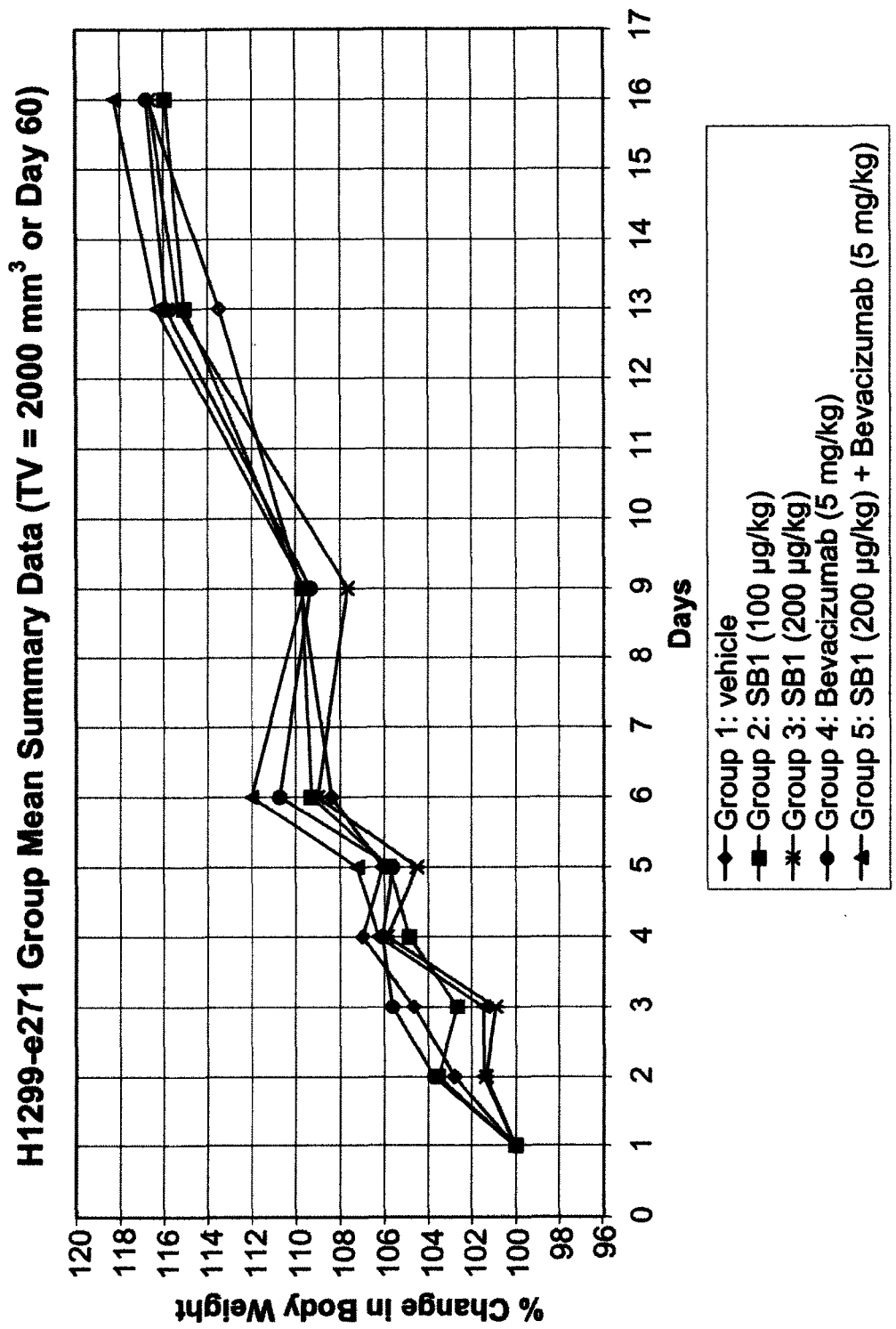
FIG. 5B shows a graph of the change in body weight over time in mice involved in a study analyzing the effect of administration of CRF, bevacizumab (Avastin®), or CRF and bevacizumab (Avastin®) on human non-small cell lung carcinoma tumor cell growth.
Figure 5C:
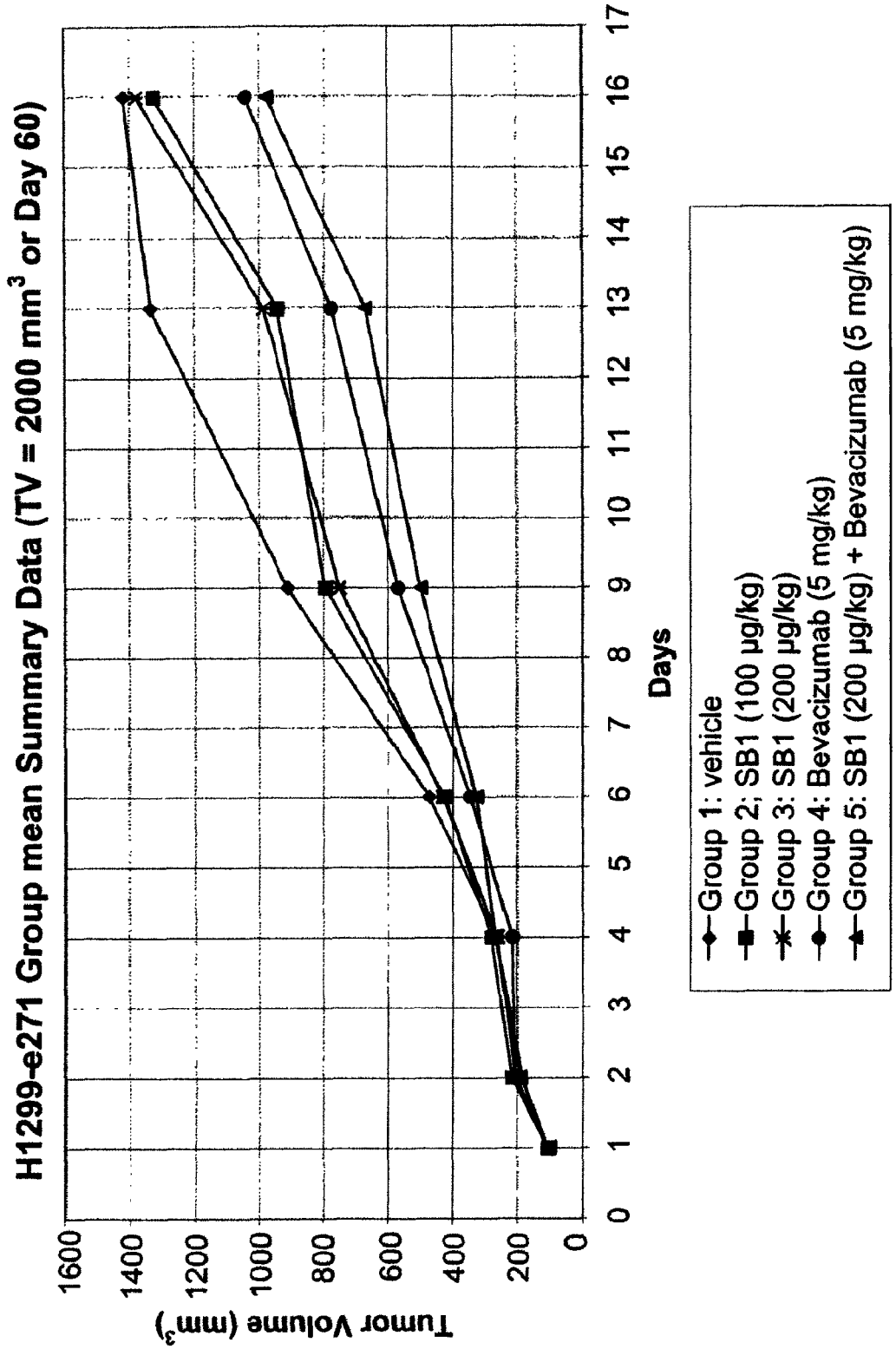
FIG. 5C shows a graph of the change in tumor volume over time in mice involved in a study analyzing the effect of administration of CRF, bevacizumab (Avastin®), or CRF and bevacizumab (Avastin®) on human non-small cell lung carcinoma tumor cell growth.
Figure 6B:
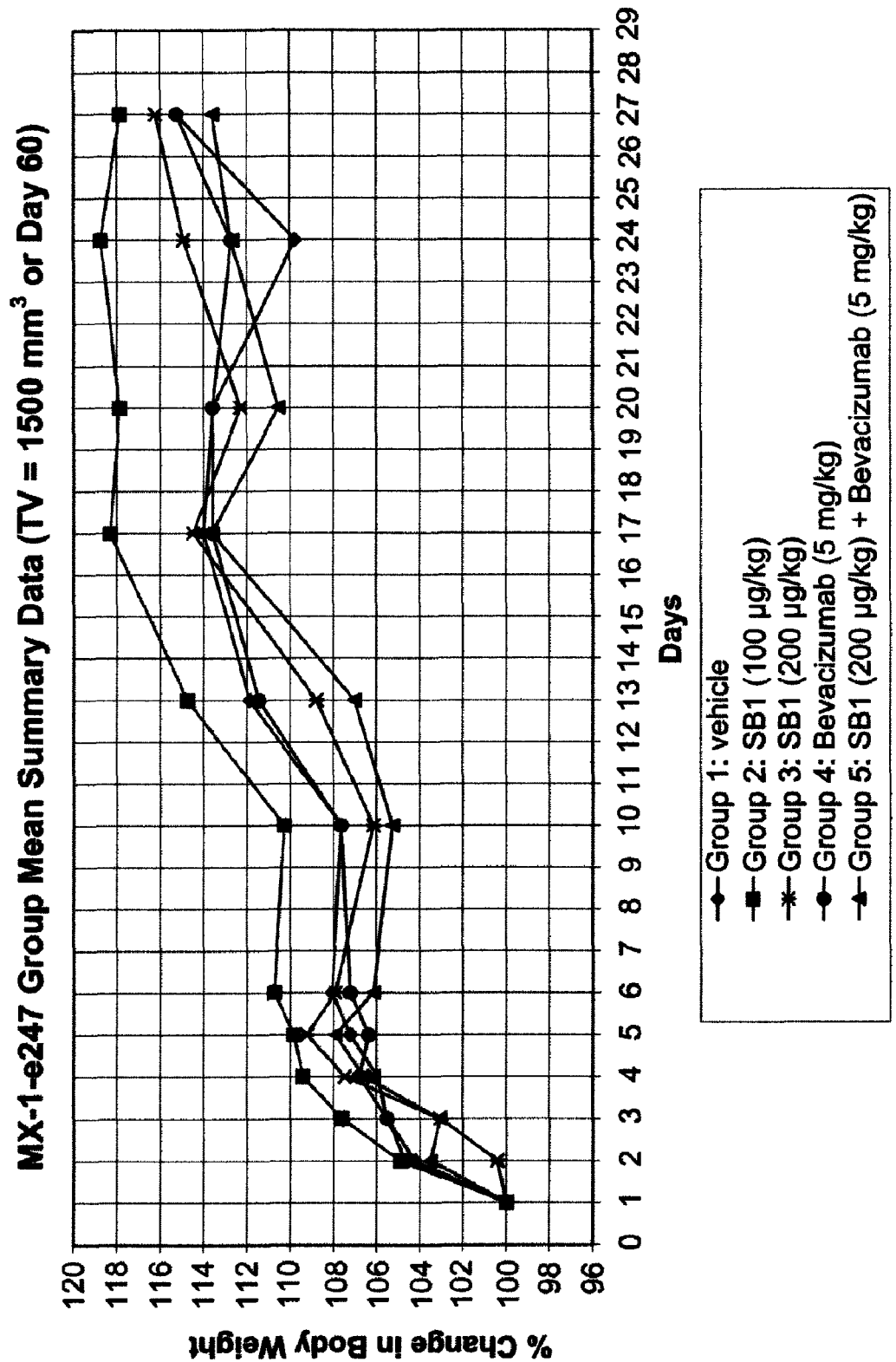
FIG. 6B shows a graph of the change in body weight over time in mice involved in a study analyzing the effect of administration of CRF, bevacizumab (Avastin®), or CRF and bevacizumab (Avastin®) on human breast carcinoma cell growth.
Figure 6C:
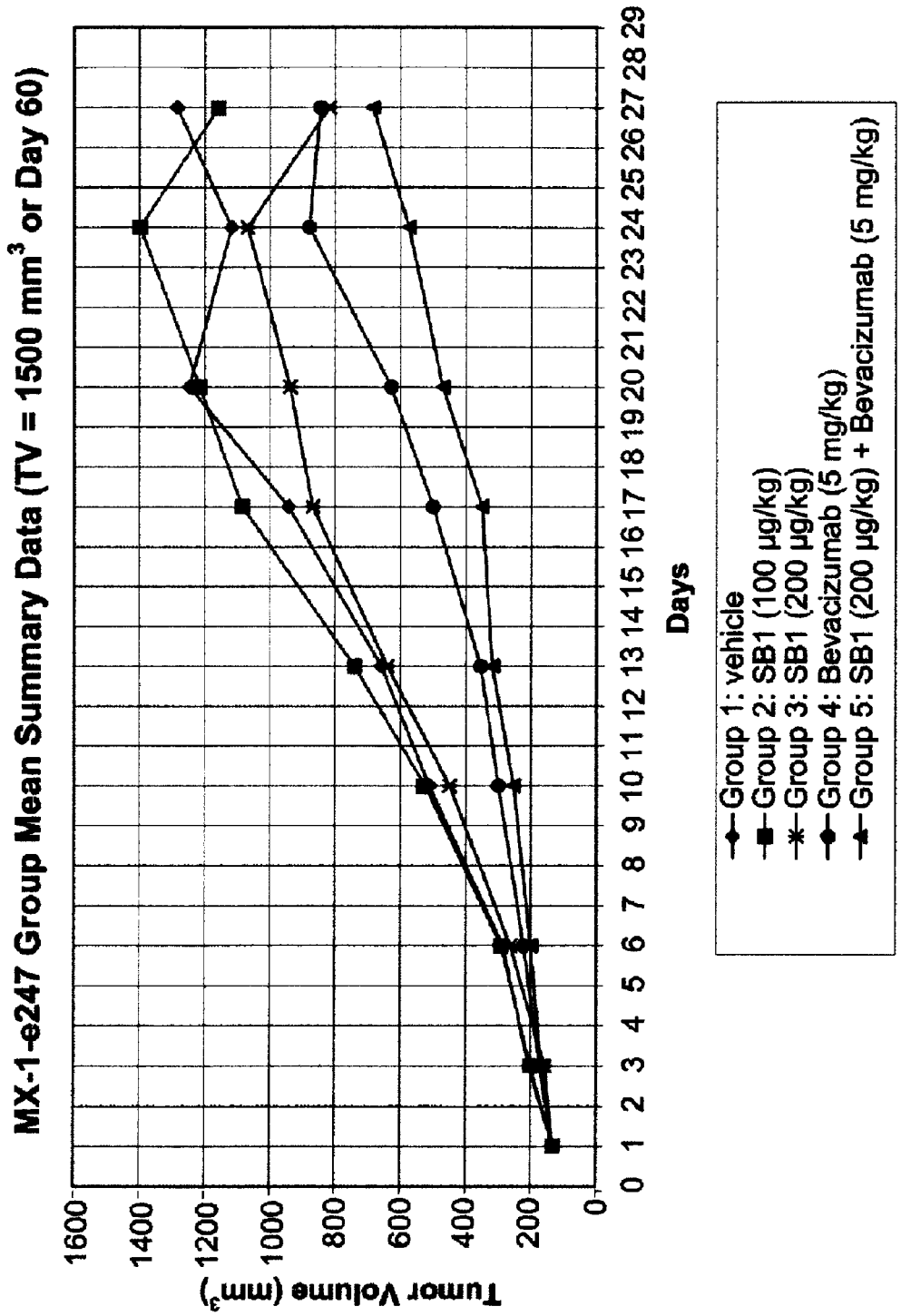
FIG. 6C shows a graph of the change in tumor volume over time in mice involved in a study analyzing the effect of administration of CRF, bevacizumab (Avastin®), or CRF and bevacizumab (Avastin®) on human breast carcinoma cell growth.

In a second study, 8-12 week old female nu/nu mice were injected with 1 mm$^3$ tumor fragments of human Non-Small Cell Lung Carcinoma (NSCLC) tumor cell lines subcutaneously. Once tumors developed and reached an average size of 80-120 mg., mice received administration of: (1) saline (control) (twice daily, subcutaneous); (2) CRF (100 µg/kg) (twice daily, subcutaneous); (3) CRF (200 µg/kg) (twice daily, subcutaneous); (4) bevacizumab (Avastin®) (5 mg/kg) (twice weekly, intraperitoneal); or (5) CRF (200 µg/kg) (twice daily, subcutaneous) and bevacizumab (Avastin®) (5 mg/kg) (twice weekly, intraperitoneal) (FIG. 5A). Body weight and tumor volume were measured twice a week until the endpoint of the experiment, i.e., the earlier of either 60 days or achieving a tumor weight of 2 g.). Results indicate that a reduction in tumor volume in mice receiving single agents as compared to control, and the most reduction in tumor volume in mice receiving a combination of CRF and bevacizumab (Avastin®) (FIGS. 5B-5D). This study suggests that the effect of administering a combination of CRF and bevacizumab (Avastin®) on inhibiting the development or growth of a lung tumor and/or on the reduction of lung tumor size great than administering either CRF alone or bevacizumab (Avastin®) alone In another study, 8-12 week old female nu/nu mice were injected with 1 mm$^3$ tumor fragments of MX-1 human breast carcinoma subcutaneously. Once tumors developed and reached an average size of 80-120 mg., mice received administration of (1) saline (control) (twice daily, subcutaneous); (2) CRF (100 µg/kg) (twice daily, subcutaneous); (3) CRF (200 µg/kg) (twice daily, subcutaneous); (4) bevacizumab (Avastin®) (5 mg/kg) (twice weekly, intraperitoneal); or (5) CRF (200 µg/kg) (twice daily, subcutaneous) and bevacizumab (Avastin®) (5 mg/kg) (twice weekly, intraperitoneal) (FIG. 6A). Body weight and tumor volume were measured twice a week until the endpoint of the experiment, i.e., the earlier of either 60 days or achieving a tumor weight of 1.5 g.). Results indicate that a reduction in tumor volume in mice receiving single agents as compared to control, and the most reduction in tumor volume in mice receiving a combination of CRF and bevacizumab (Avastin®) (FIGS. 6B-6D). This study suggests that the effect of administering a combination of CRF and bevacizumab (Avastin®) on inhibiting the development or growth of a breast tumor and/or on the reduction of breast tumor size great than administering either CRF alone or bevacizumab (Avastin®) alone.

7.3 Clinical Studies

This example demonstrates that cancer patients treated with CRF for 3-6 months or longer exhibit dramatic improvement halting tumor progression and in survival.

Patients with malignant brain tumor were treated with 2 mg/day (1 mg dose, twice daily) of either human CRF subcutaneously. Patients receiving CRF either maintained tumor size or exhibited reduction in tumor size, as compared to control patients (FIG. 1). Specifically, of the 20 patients receiving CRF depicted in FIG. 1, 6 patients exhibited a reduction in tumor size while 5 patients exhibited a maintenance in tumor size. Notably, 3 of the 20 patients depicted exhibit a reduction in tumor size by over 50% after 9 months of treatment with CRF. Also, of the 10 patients receiving CRF depicted in FIG. 2, 8 exhibited a reduction in tumor size at the last time point measured. Significantly, two of the patients exhibited a reduction in tumor size of around 90%. Additionally, of the 30 patients who had received treatment for at least 6 months, 10 experienced a decrease in tumor size.

Figure 2:
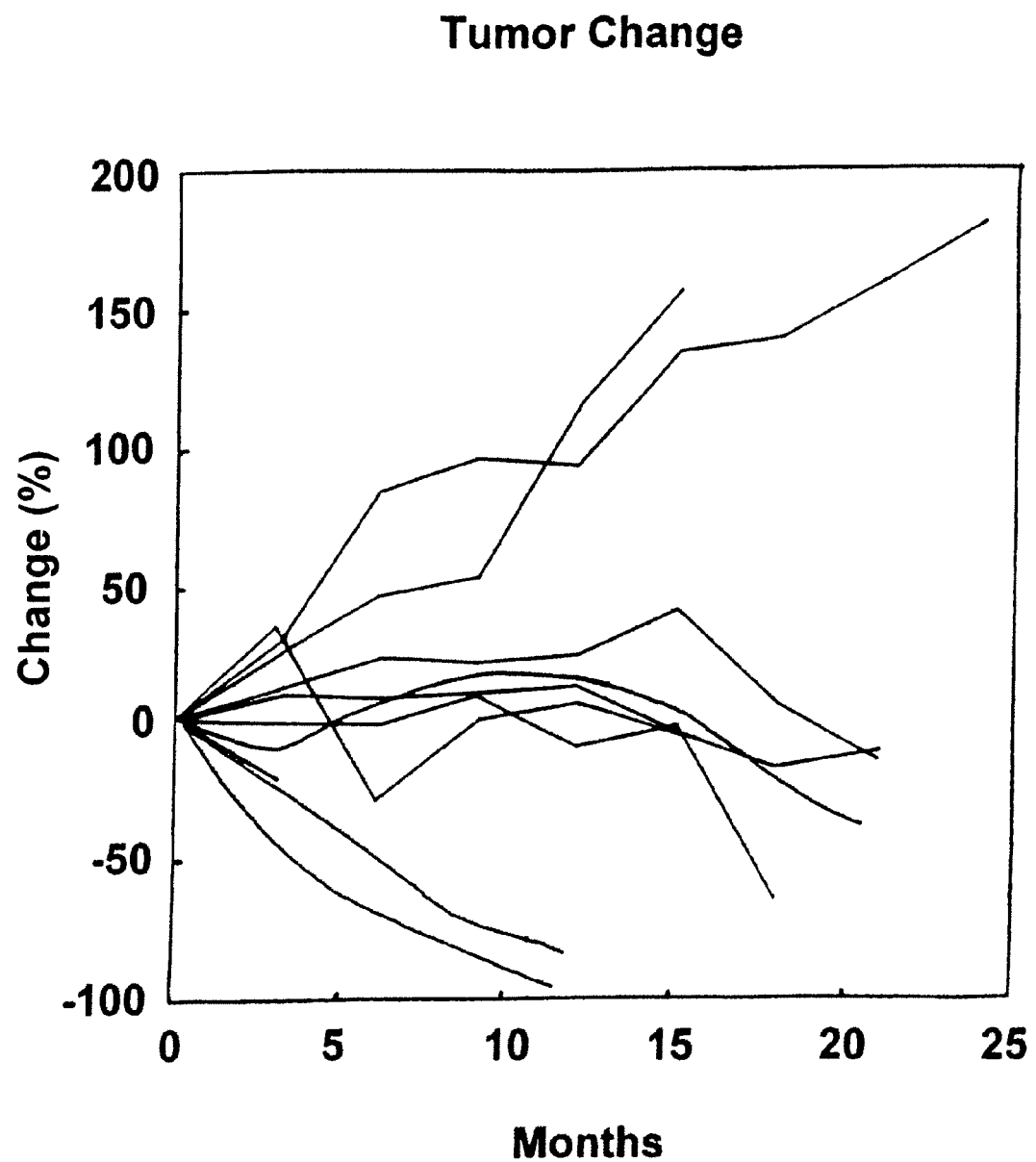
FIG. 2 shows a graph of the percent change in brain tumor size as measured by MRI in brain cancer patients receiving 2 mg/day (1 mg dose, twice daily) of human CRF subcutaneously for at least 3-6 months.

Moreover, patients receiving CRF exhibit prolonged survival. Typically, patients enrolled in these studies are not generally expected to show survival beyond 3-6 months. As shown in FIGS. 1 and 2, the overwhelming majority of patients receiving CRF live well beyond the projected 3-6 months, with some even surviving to 1-2 years after CRF treatment.

Figure 3:
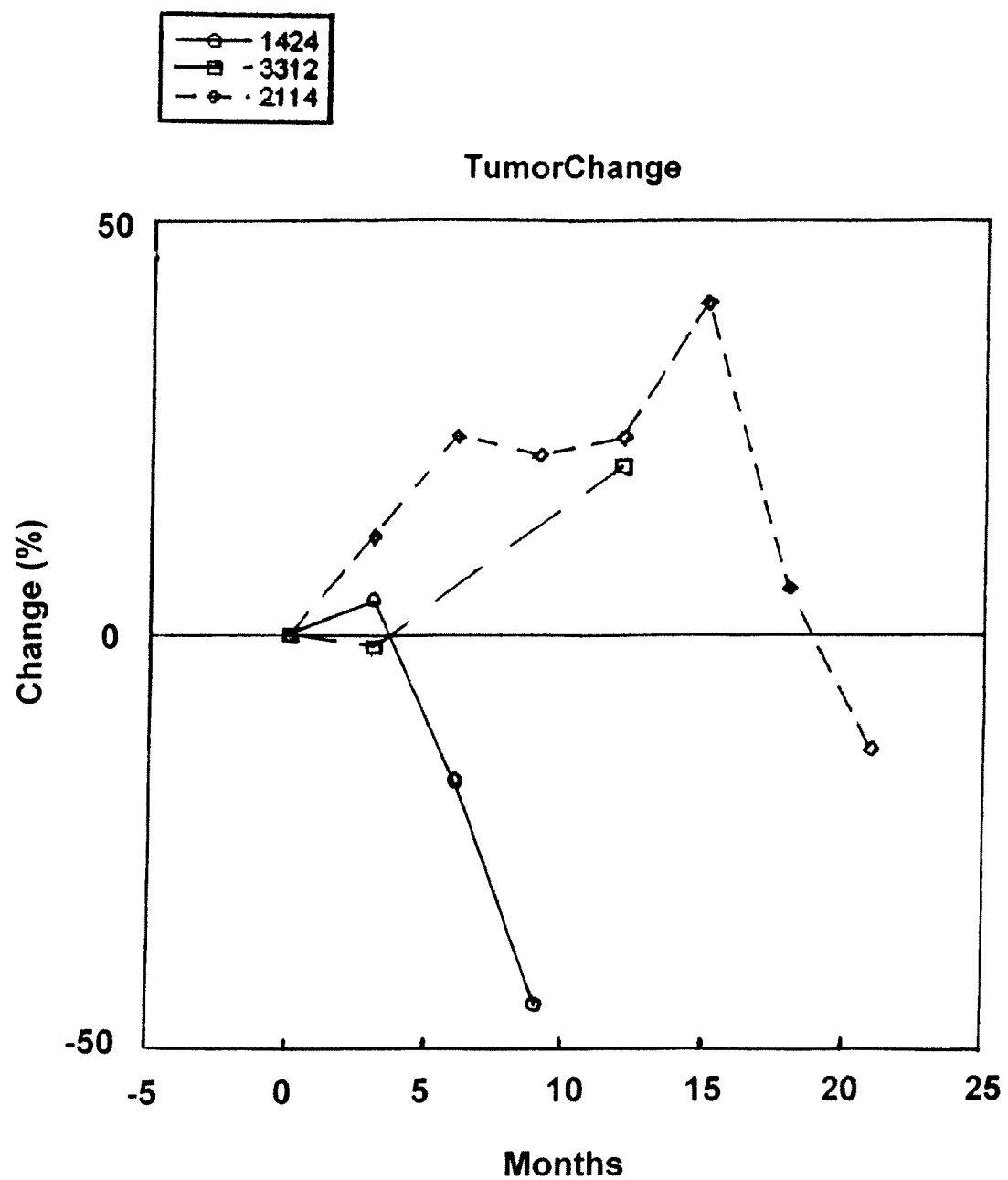
FIG. 3 shows a graph of the percent change in brain tumor size as measured by MRI in metastatic patients receiving 2 mg/day (1 mg dose, twice daily) of hCRF subcutaneously for at least 3-6 months.

In particular, metastatic patients responded very favorably to CRF treatment. Of the 3 metastatic patients receiving CRF depicted in FIG. 3, 2 showed a reduction in tumor size at the last timepoint measured, and all 3 exhibited survival beyond the projected 3-6 months.

8. EQUIVALENTS

The present disclosure is not to be limited in scope by the specific embodiments described which are intended as single illustrations of individual aspects of the disclosure, and functionally equivalent methods and components are within the scope of the disclosure. Indeed, various modifications of the disclosure, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present disclosure.

The invention claimed is:

1. A method for inhibiting tumor progression in a human patient with cancer, comprising administering human corticotropin-releasing factor (CRF) and bevacizumab to said patient; wherein said administering CRF comprises administering CRF to said patient subcutaneously at least once per day, wherein the cancer is breast cancer or colon cancer.

2. The method of claim 1, wherein the cancer is metastatic.

3. The method of claim 1, wherein the method further comprises monitoring tumor progression in the human.

4. The method of claim 1, wherein said administering CRF comprises administering CRF in a dose between 1 µg/kg to 100 µg/kg of body weight of the patient.

5. The method of claim 1, wherein said administering CRF comprises administering CRF in a dose of about 1 to about 4 mg.

6. The method of claim 1, wherein said administering CRF comprises administering CRF in a dose of about 1 mg.

7. The method of claim 1, wherein said administering CRF comprises administering CRF twice daily to said patient.

8. The method of claim 1, wherein said administering CRF comprises administering CRF to said patient at least once a day for a period of 2 weeks or more.

9. The method of claim 1, wherein said administering CRF comprises administering CRF to said patient at least once a day for a period of one month or more.

10. The method of claim 1, wherein said administering CRF comprises administering CRF to said patient at least once a day for a period of 3 months or more.

11. The method of claim 1, wherein bevacizumab is administered in a dose between 5 mg/kg and 15 mg/kg of body weight of the patient.

12. The method of claim 1, wherein bevacizumab is administered in a dose of 10 mg/kg of body weight of the patient.

13. The method of claim 1, wherein said administering bevacizumab is administered to the patient once a week, every two weeks or every three weeks.

14. The method of claim 1, wherein the cancer is breast cancer.

15. The method of claim 1, wherein the cancer is colon cancer.

* * * * *